(12) United States Patent
Pilarski et al.

(10) Patent No.: US 6,416,948 B1
(45) Date of Patent: *Jul. 9, 2002

(54) METHODS FOR DETECTION OF REARRANGED DNA

(75) Inventors: Linda M. Pilarski, Stony Plain; Andrew R. Belch; Agnieszka J. Szczepek, both of Edmonton, all of (CA)

(73) Assignee: The Governors of the University of Alberta, Edmonton (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,842

(22) PCT Filed: Jun. 3, 1997

(86) PCT No.: PCT/US97/09534

§ 371 (c)(1),
(2), (4) Date: Apr. 1, 1999

(87) PCT Pub. No.: WO97/46706

PCT Pub. Date: Dec. 11, 1997

Related U.S. Application Data

(60) Provisional application No. 60/019,106, filed on Jun. 3, 1996.

(51) Int. Cl.[7] .............................. C12Q 1/68; C12P 19/31
(52) U.S. Cl. .......................... 435/6; 435/91.1; 435/91.2
(58) Field of Search ........................... 435/6, 91.2, 810, 435/91.1; 536/24.31, 24.33

(56) References Cited

U.S. PATENT DOCUMENTS

| | | | |
|---|---|---|---|
| 4,683,202 A | | 7/1987 | Mullis .......................... 435/91 |
| 5,024,934 A | * | 6/1991 | Lee ................................ 435/6 |
| 5,418,134 A | | 5/1995 | Morley et al. ................. 435/6 |
| 5,436,144 A | | 7/1995 | Stewart et al. .............. 435/91.2 |

OTHER PUBLICATIONS

Pilarski et al. Blood. Nov. 1995. 86: 58a, abstract 219.*
Ghali. Blood. 85: 2795–2801, May 1995.*
Embleton et al. Nucleic Acids Research. 20: 3831–3837, 1992.*
Bakkus, M.H.C. et al., "Evidence that clonogenic cell in multiple myeloma originates from a pre-switched but somatically mutated B cell," *Brit. J. Henatol.*, 87:68 (1994).
Barlogie, B. et al., "Plasma cell myeloma: New biological insights and advances in therapy," *Blood*, 73:865 (1989).
Berenson, J. et al., "Evidence of peripheral blood B lymphocyte but not T lymphocyte involvement in multiple myeloma," *Blood*, 70:1550 (1987).
Bergsagel, D.E., "Treatment of plasma cell myeloma," *Ann. Rev. Med.*, 30:431 (1979).

Bergsagel, P.L. et al., "In multiple myeloma, clonotypic B lymphocytes are detectable among CD19+ peripheral blood cells expressing CD38, CD56 and monotypic immunoglobulin light chain," *Blood.* 85:436 (1995).
Billadeau, D. et al., "Analysis of B–lymphoid malignancies using allele–specific polymerase chain reaction: A technique for sequential quantitation of residual disease," *Blood*, 78:3021 (1991).
Billadeau, D. et al., "Detection and quantitation of malignant cells in the peripheral blood of multiple myeloma patients," *Blood*, 80:1818 (1992).
Billadeau, D. et al. "The bone marrow of multiple myeloma patients contains B cell populations at different stages of differentiation that are clonally related to the malignant plasma cell," *J. Exp. Med.*, 178:1023 (1993).
Billadeau, D. et al., "Clonal circulating cells are a common occurrence in plasma cell disorders: A comparison of MGUS, SMM and MM," *Blood*, 86:58a (1995).
Boccadoro, M. et al., "Kinetics of circulating B lymphocytes in human myeloma," *Blood*, 61:812 (1983).
Caligaris–Cappio, F et al., "Identification of malignant plasma cell precursors in the bone marrow of multiple myeloma," *J. Clin. Invest.*, 76:1243 (1985).
Cao, J. et al. "Identification of malignant cells in multiple myeloma bone marrow with immunoglobulin Vh gene probes by fluorescent in situ hybridization and flow cytometry," *J. Clin. Invest.*, 95:964 (1995).
Cao, J. et al. A CD10–positive subset of malignant cells is identified in multiple myeloma using PCR with patient–specific immunoglobulin gene primers, *Leukemia*, 9:1948 (1995).

(List continued on next page.)

Primary Examiner—Carla J. Myers
(74) Attorney, Agent, or Firm—Lahive & Cockfield, LLP; Giulio A. DeConti, Jr.

(57) ABSTRACT

The invention provides methods for the identification of members of a malignant lymphocyte clone by analysis of clonotypic DNA rearrangements of T cell or B cell receptor genes. The DNA or RNA from isolated single tumor cells is amplified by PCR using consensus primers to the VDJ region of the receptor genes, and the sequence of the VDJ region is obtained from each. The clonotypic sequence of the malignant clone is identified as the most frequent VDJ sequence amplified. Individual-specific PCR primers for the VDJ region are then designed based upon the clonotypic sequence. These specific PCR primers are used to detect and quantitate clonotypic cells in subsequent patient samples using in situ PCR or in situ RT-PCR. Fractionated or unfractionated samples of blood or bone marrow, as well as tissue sections can be analyzed. The methods provide a highly sensitive and quantitative means to monitor the progress of disease and the efficacy of treatment protocols, as well as to detect members of the malignant clone in autologous bone marrow cells destined for transplant.

19 Claims, 10 Drawing Sheets

OTHER PUBLICATIONS

Cassel, A. et al., evidence for the existence of circulating monoclonal b–lymphocytes in multiple myeloma patients, *Exp. Hematol.,* 18:1171 (1990).

Chen, B.J. et al. "Circulating clonal lymphocytes in myeloma constitute a minor population of B cells," *Blood,* 87:1972 (1996).

Claxton, D.F. et al., "Detection of fusion transcripts generated by the inversion 16 chromosomes in acute myelogenous leukemia," *Blood,* 83:1750–1756 (1994).

Corradini, P. et al., "High dose sequential chemotherapy in multiple myeloma: Residual tumor cells are detectable in bone marrow and peripheral blood cell harvests and after autografting," *Blood,* 85:1596 (1995).

Corradini, P. et al. "Detection of circulating tumor cells in multiple myeloma by a PCR based method," *Leukemia*7:1879 (1993).

Davies, T.H. et al., "Detection of clonal immunoglobulin gene rearrangements by polymerase chain reaction amplification and single–strand conformational polymorphism analysis," *Am. J. Pathology,* 42(6):1841–1847 (1993).

Dreyfus, F. et al. "Contamination of peripheral blood by monoclonal B cells following treatment of multiple myeloma by high dose chemotherapy," *Brit. J. Hematol.,* 85:411 (1993).

Gazitt, U. et al., "Differential peripheral blood mobilization of tumor and normal hematopoietic progenitor cells (HPC) in multiple myeloma (MM)," *Blood,* 84:354a (1994).

Greipp, P.R., "Advances in the diagnosis and management of myeloma," *Sem. Hetamol.,* 29:24 (1992).

Hulin, N. et al., "Biology of the human myeloma population," *La Ricerca in Clinica e in Laboratorio,* 8:49 (1978).

Jensen, G.S. et al., "Selective expression of CD45 isoforms CALLA+ monoclonal B lineage cells in peripheral blood from myeloma patients as late stage B cells," *Blood,* 78:711 (1991).

Mariette, X. et al., "Myeloma cell contamination of peripheral blood stem cell grafts in patients with multiple with multiple myeloma treated by high dose therapy," *Bone Marrow Transp.,* 14:47 (1994).

Omede, P. et al., "Multiple myeloma: "Early" plasma cell phenotype identifies patients with aggressive biological and clinical characteristics," *Brit. J. Henatol.,* 85:504 (1993).

Owen, R.G. et al., "Detection of contaminating cells in PBMC harvests and the efficacy of CD34 selection in patients with multiple myeloma," *Blood,* 84:352a (1994).

Palmer, M. et al., "Reassessment of the relationship between M–protein decrement and survival in multiple myeloma," *Br. J. Cancer,* 59:110 (1989).

Pietersz, G.A. et al., "In vitro and in vivo antitumor–activity of a chimeric anti–CD19 antibody," *Cancer Immunol. Immunother,* 41:53 (1995).

Pilarski, L.M. et al., "Severe deficiency of B lymphocytes in peripheral blood from multiple myeloma patients," *J. Clin. Invest.,* 74:1301 (1984).

Pilarski, L.M. et al., "Abnormal function of B lymphocytes from peripheral blood of multiple myeloma patients. I. Lack of correlation between the number of cells potentially able to secrete IgM and serum IgM levels," *J. Clin. Invest.,* 75:2024 (1985).

Pilarski, L.M. et al., "Monoclonal circulating B cells in multiple myeloma: A continuously differentiating possibly invasive population as defined by expression of CD45 isoforms and adhesion molecules," *Hematology/Oncology Clinics of North America,* 6:297 (1992).

Pilarski, L.M. et al., "Circulating monoclonal B cells expressing p–glycoprotein may be a reservoir of multidrug resistant disease multiple myeloma," *Blood,* 83:724 (1994).

Pilarski, L.M. et al., "Circulating clonotypic B cells in the biology of myeloma. Speculations on the origin of multiple myeloma," *Leuk. Lymphoma,* 18:179 (1996).

Rowley, J.D., "Molecular cytogenetics: Rosetta Stone for understanding cancer–twenty–ninth G.H.A," Clowes Memorial Award Lecture, *Cancer Res.,* 50:3816–3825 (1990).

Socie, J. et al., "Studies on hemopoietic chimerism following allogeneic bone marrow transplantation in the molecular biology era," *Leukemia Research,* 19:497–504 91995).

Takashita, M. et al., "Cellular origin and extent of clonal involvement in multiple myeloma: genetic and phenotypic studies," *Brit. J. Haematol.,* 87:735 (1994).

Taub, R. et al., "Translocation of the c–myc gene into the immunoglobulin heavy chain locus in human burkitt lymphoma and murine plasmacytoma cell," *PNAS USA,* 79:7837 (1982).

Vescio, R.A. et al., "Quantitative comparison of multiple myeloma contamination in bone marrow harvest and leukaphereses autografts," *Blood,* 86:234a (1995).

Yameda, M. et al., "Minimal residual disease in childhood B–lineage lymphoblastic leukemia," *N. Eng. J. Med.,* 323:448 (1990).

Zola, H. et al., "Preparation and characterization of a chimeric CD19 monoclonal antibody," *Immunol. Cell Biol.,* 69:411 (1991).

* cited by examiner

```
                                        150       160       170       180       190       200
                                        I         I         I         I         I         I
DP-31                           ...gtctcaggtattagttggaatagtggtagcataggctatgcggactctgtgaagggccgattcaccatctcc
JOD-5 B2.1    FR2 primer........................cg...........g..c..tc...a....t...........c.g.................
JOD-5 B3.3    FR2 primer........................cg...........g..c..tc...a....t...........c.g.................
JOD-5 BM 1.9  FR2 primer........................cg...........g..c..tc...a....t...........c.g.................
JOD-5 BM 4.4  FR2 primer........................cg...........g..c..tc...a....t...........c.g.................
consesnsus                              GTCTCAAGTATTACGTGGAATAGGGGCCAGTCTAGGATATGTGGACTCTGTCAGGGGCCGATTCACCATCTCC 210       220       230       240       250       260       270       280
          I         I         I         I         I         I         I         I
..........I.........I.........I.........I.........I.........I.........I.........I
agagacaacgccaagaactccctgtatctgcaaatgaacagtctgagagctgaggacacggcctgtattactgtgcaaaa
.a......g..tg......g.t.....................................a..............t....g.........
.a......g..tg..c..g.t.....................................a..............t....g.........
.a......g..tg......g.t.....................................a..............t....g.........
.a......g..tgt.....g.t.......................................................t.tgtt...g.........
AAAGACAGCGTGAAGAAGTTCCTGTATCTGCAAATGAACAGTCTGAGAACTGAGAAGACAGTCTGAGAACTGAGGACACGGCCTTGTATTATTGTGTAAAGCCGAGATGGCTACAACTTCGAAGGACAACA..JH2
```

Fig. 3A

```
consensus            GTCTCAAGTATTACGTGGAATAGGGGCAGTCTCTAGGATATGTGGACTCTGTCAGGGGCCGATTCACCATCTCC
JOD-5 BM 5.3   FR2 primer......A.CGTCTCCT.AG.TGGATCCC.T.CCTGG..CC.A.GGACTGG.CA.GGATC.C.TAA.CTT..GAAT
JOD-5 B 6.1    FR2 primer.. TCAC.GTC.TA.GAA.TCGGA.A....CTGGAGT.G.CACC.TCTC..CAGGT..AT.CCG.ACTGGGC.A
JOD-5 BM 1.9   FR2 primer...........................................................................

AAGACAGCGTGAAGAAGTTCCTGTATCTGCAAATGAACAGTCTGAGGAACTGAGGACACGGCCCTTGTATTATTGTGTAAAGGCCGAGATGGCTACAACTTCGAAGGAC
TC.GA.AG.GCCT.G...GGG.C.CAAGTATT.C.TGG.A.AG.G.C.G.CTA.GATATGTGGAC.C.GTCA.G.GCCGATTCACC..C
.G.C.CCTG.T.AC.GA.C.G.TATGAATTCGGAA.GGGCCTG.A.TTG.C.CGT.TTCCT.AA.GTGG.TCCC.T..CCTTATGA.TTCGAAAGGGCCTGAGTGGTCACCGTCT
...........................................................................................
```

Fig. 3B

```
CONS.  TGGAATAGGGGCAGTCTAGGATATGTGGACTCTGTCAGGGGCCGATTCACCATCTCCA
JOD6B1 ..........................................................
JOD6B2 ..........................................................
JOD6B3 ..........................................................
JOD6B4 ..........................................................
JOD6B5 ..........................................................
JOD5BM ..........................................................
       .|.........|.........|.........|.........|.........|.........|....
        10        20        30        40        50        60        70

CONS.  AAGACAGCGTGAAGAAGTTCCTGTATCTGCAAATGAACAGTCTGAGAACTGAGGACACGGCCT
JOD6B1 ................................................................
JOD6B2 ................................................................
JOD6B3 ................................................................
JOD6B4 ........A.......................................................
JOD6B5 ........A.......................................................
JOD5BM ........TG......................................................
       .....|.........|.........|.........|.........|.........|.........|
            80        90       100       110       120       130       140
```

Fig. 4B

Sequence of LAR VDJ:

```
                   ——————— CDR2 PRIMER ———————
5'... CTT GGG ACT TCT ACG ACA ATG GCG AAA CCT TCA ACA ATC CGT CCT

CAC GGG TGG TCG AGT CAC CGT GTC CCT AGA CAC ATC TCA GAA TTA TTT GTC

CCT GGA AGT AGT CTC TGT GAA CGC CGC AGA CAC GGG TAT TTA TTA CTG TGC

GGG TGG CAC CAC GTC CTC CCA GGG TCA GAG GTT GGA ATC ...3'
              ——————— CDR3 PRIMER ———
```

Fig. 5B

SEQUENCE LISTING

```
<160> NUMBER OF SEQ ID NOS: 76

<210> SEQ ID NO 1
<211> LENGTH: 20
<212> TYPE: DNA
<213> ORGANISM: Homo sapiens

<400> SEQUENCE: 1
ccactgaact tctgattcgc                                                    20

<210> SEQ ID NO 2
<211> LENGTH: 20
<212> TYPE: DNA
<213> ORGANISM: Homo sapiens

<400> SEQUENCE: 2
gcgtgctagc tggatgtctt                                                    20

<210> SEQ ID NO 3
<211> LENGTH: 20
<212> TYPE: DNA
<213> ORGANISM: Homo sapiens

<400> SEQUENCE: 3
gacctcacca tggcccctgg                                                    20

<210> SEQ ID NO 4
<211> LENGTH: 18
<212> TYPE: DNA
<213> ORGANISM: Homo sapiens

<400> SEQUENCE: 4
cagccagtgc catagtac                                                      18

<210> SEQ ID NO 5
<211> LENGTH: 27
<212> TYPE: DNA
<213> ORGANISM: Homo sapiens

<400> SEQUENCE: 5
tatgaattcg gaaagggcct ggagtgg                                            27

<210> SEQ ID NO 6
<211> LENGTH: 28
<212> TYPE: DNA
<213> ORGANISM: Homo sapiens

<400> SEQUENCE: 6
acgggatcca cctgaggaga cggtgacc                                           28

<210> SEQ ID NO 7
<211> LENGTH: 32
<212> TYPE: DNA
<213> ORGANISM: Homo sapiens
<220> FEATURE:
<221> NAME/KEY: misc_feature
<222> LOCATION: 20
<223> OTHER INFORMATION: n = a, c, g, or t

<400> SEQUENCE: 7
acggatccgt gaccagggtn ccttggcccc ag                                      32
```

```
<210> SEQ ID NO 8
<211> LENGTH: 18
<212> TYPE: DNA
<213> ORGANISM: Homo sapiens

<400> SEQUENCE: 8
cgtggaatag gggcagtc                                                 18

<210> SEQ ID NO 9
<211> LENGTH: 18
<212> TYPE: DNA
<213> ORGANISM: Homo sapiens

<400> SEQUENCE: 9
aagttgtagc catctcgg                                                 18

<210> SEQ ID NO 10
<211> LENGTH: 22
<212> TYPE: DNA
<213> ORGANISM: Homo sapiens

<400> SEQUENCE: 10
acttctacga caatggcgaa ac                                            22

<210> SEQ ID NO 11
<211> LENGTH: 18
<212> TYPE: DNA
<213> ORGANISM: Homo sapiens

<400> SEQUENCE: 11
ccctccgagg acgtggtg                                                 18

<210> SEQ ID NO 12
<211> LENGTH: 9
<212> TYPE: DNA
<213> ORGANISM: Homo sapiens

<400> SEQUENCE: 12 tgtgctcac                                                            9

<210> SEQ ID NO 13
<211> LENGTH: 9
<212> TYPE: DNA
<213> ORGANISM: Homo sapiens

<400> SEQUENCE: 13 tgtgcgaca                                                            9

<210> SEQ ID NO 14
<211> LENGTH: 9
<212> TYPE: DNA
<213> ORGANISM: Homo sapiens

<400> SEQUENCE: 14 tgtgcgaga                                                            9

<210> SEQ ID NO 15
<211> LENGTH: 9
<212> TYPE: DNA
<213> ORGANISM: Homo sapiens

<400> SEQUENCE: 15 tgtgcgggt                                                            9
```

-continued

```
<210> SEQ ID NO 16
<211> LENGTH: 9
<212> TYPE: DNA
<213> ORGANISM: Homo sapiens

<400> SEQUENCE: 16 tgtgcgaag                                                                 9

<210> SEQ ID NO 17
<211> LENGTH: 9
<212> TYPE: DNA
<213> ORGANISM: Homo sapiens

<400> SEQUENCE: 17 tgtgcgagg                                                                 9

<210> SEQ ID NO 18
<211> LENGTH: 9
<212> TYPE: DNA
<213> ORGANISM: Homo sapiens

<400> SEQUENCE: 18 tgtgcgaga                                                                 9

<210> SEQ ID NO 19
<211> LENGTH: 9
<212> TYPE: DNA
<213> ORGANISM: Homo sapiens

<400> SEQUENCE: 19 tgtgcgaga                                                                 9

<210> SEQ ID NO 20
<211> LENGTH: 9
<212> TYPE: DNA
<213> ORGANISM: Homo sapiens

<400> SEQUENCE: 20 tgtgcgaga                                                                 9

<210> SEQ ID NO 21
<211> LENGTH: 9
<212> TYPE: DNA
<213> ORGANISM: Homo sapiens

<400> SEQUENCE: 21 tgttcacac                                                                 9

<210> SEQ ID NO 22
<211> LENGTH: 9
<212> TYPE: DNA
<213> ORGANISM: Homo sapiens

<400> SEQUENCE: 22 tgtgcgcca                                                                 9

<210> SEQ ID NO 23
<211> LENGTH: 9
<212> TYPE: DNA
<213> ORGANISM: Homo sapiens

<400> SEQUENCE: 23 tgtaccaca                                                                 9
```

```
<210> SEQ ID NO 24
<211> LENGTH: 9
<212> TYPE: DNA
<213> ORGANISM: Homo sapiens

<400> SEQUENCE: 24 tgtgcgaca                                                          9

<210> SEQ ID NO 25
<211> LENGTH: 9
<212> TYPE: DNA
<213> ORGANISM: Homo sapiens

<400> SEQUENCE: 25 tgtacgaga                                                          9

<210> SEQ ID NO 26
<211> LENGTH: 9
<212> TYPE: DNA
<213> ORGANISM: Homo sapiens

<400> SEQUENCE: 26 tgcgccaca                                                          9

<210> SEQ ID NO 27
<211> LENGTH: 9
<212> TYPE: DNA
<213> ORGANISM: Homo sapiens

<400> SEQUENCE: 27 tgtgcgaca                                                          9

<210> SEQ ID NO 28
<211> LENGTH: 9
<212> TYPE: DNA
<213> ORGANISM: Homo sapiens

<400> SEQUENCE: 28 tgtactaga                                                          9

<210> SEQ ID NO 29
<211> LENGTH: 9
<212> TYPE: DNA
<213> ORGANISM: Homo sapiens

<400> SEQUENCE: 29 tgtgcgaga                                                          9

<210> SEQ ID NO 30
<211> LENGTH: 30
<212> TYPE: DNA
<213> ORGANISM: Homo sapiens

<400> SEQUENCE: 30
aaacttatca ctggttggga cggtagtagt                                   30

<210> SEQ ID NO 31
<211> LENGTH: 18
<212> TYPE: DNA
<213> ORGANISM: Homo sapiens

<400> SEQUENCE: 31
```

-continued caacactact atgatagt                                                 18

<210> SEQ ID NO 32
<211> LENGTH: 33
<212> TYPE: DNA
<213> ORGANISM: Homo sapiens

<400> SEQUENCE: 32
gatacctatt attatggttc agggagttat tca                                33

<210> SEQ ID NO 33
<211> LENGTH: 21
<212> TYPE: DNA
<213> ORGANISM: Homo sapiens

<400> SEQUENCE: 33
ggcaccacgt cctcccaggg t                                             21

<210> SEQ ID NO 34
<211> LENGTH: 33
<212> TYPE: DNA
<213> ORGANISM: Homo sapiens

<400> SEQUENCE: 34
ctcgtggttg tggcggtgga agctctaacc cat                                33

<210> SEQ ID NO 35
<211> LENGTH: 36
<212> TYPE: DNA
<213> ORGANISM: Homo sapiens

<400> SEQUENCE: 35
gtccccatga actatgctat aaggggaaac ttaggt                             36

<210> SEQ ID NO 36
<211> LENGTH: 33
<212> TYPE: DNA
<213> ORGANISM: Homo sapiens

<400> SEQUENCE: 36
gaatggtcgt acttctatga aagttattgg tta                                33

<210> SEQ ID NO 37
<211> LENGTH: 27
<212> TYPE: DNA
<213> ORGANISM: Homo sapiens

<400> SEQUENCE: 37
gacggaagca gagatggcta caactcg                                       27

<210> SEQ ID NO 38
<211> LENGTH: 24
<212> TYPE: DNA
<213> ORGANISM: Homo sapiens

<400> SEQUENCE: 38
ggggatggtt cgggagagat cttt                                          24

<210> SEQ ID NO 39
<211> LENGTH: 33
<212> TYPE: DNA
<213> ORGANISM: Homo sapiens

<400> SEQUENCE: 39

```
acgcgtttca tgcctgcgga tgtgaacaac ttc                            33
```

<210> SEQ ID NO 40
<211> LENGTH: 18
<212> TYPE: DNA
<213> ORGANISM: Homo sapiens

<400> SEQUENCE: 40

```
gttcttgcca actggttt                                             18
```

<210> SEQ ID NO 41
<211> LENGTH: 21
<212> TYPE: DNA
<213> ORGANISM: Homo sapiens

<400> SEQUENCE: 41

```
gcgttcagtg agccctccag c                                         21
```

<210> SEQ ID NO 42
<211> LENGTH: 30
<212> TYPE: DNA
<213> ORGANISM: Homo sapiens

<400> SEQUENCE: 42

```
gatcaagatg actacggtga ctacgggacc                                30
```

<210> SEQ ID NO 43
<211> LENGTH: 36
<212> TYPE: DNA
<213> ORGANISM: Homo sapiens

<400> SEQUENCE: 43

```
gtaaatcctt tctatgaagg tagtcgttat cccata                         36
```

<210> SEQ ID NO 44
<211> LENGTH: 12
<212> TYPE: DNA
<213> ORGANISM: Homo sapiens

<400> SEQUENCE: 44

```
gatccctctg ac                                                   12
```

<210> SEQ ID NO 45
<211> LENGTH: 36
<212> TYPE: DNA
<213> ORGANISM: Homo sapiens

<400> SEQUENCE: 45

```
gtaaatcctt tctatgaagg tagtcgttat cccata                         36
```

<210> SEQ ID NO 46
<211> LENGTH: 54
<212> TYPE: DNA
<213> ORGANISM: Homo sapiens

<400> SEQUENCE: 46

```
gatagggagg atactgtagt aggaacagtt actatgggcc gaatacccac ggtt     54
```

<210> SEQ ID NO 47
<211> LENGTH: 15
<212> TYPE: DNA
<213> ORGANISM: Homo sapiens -continued

```
<400> SEQUENCE: 47
cattatcacg gttac                                                        15

<210> SEQ ID NO 48
<211> LENGTH: 18
<212> TYPE: DNA
<213> ORGANISM: Homo sapiens

<400> SEQUENCE: 48
tactttgacc agtggggc                                                     18

<210> SEQ ID NO 49
<211> LENGTH: 18
<212> TYPE: DNA
<213> ORGANISM: Homo sapiens

<400> SEQUENCE: 49
tatattgact tctggggc                                                     18

<210> SEQ ID NO 50
<211> LENGTH: 24
<212> TYPE: DNA
<213> ORGANISM: Homo sapiens

<400> SEQUENCE: 50
tactggtact tcgatctctg gggc                                              24

<210> SEQ ID NO 51
<211> LENGTH: 21
<212> TYPE: DNA
<213> ORGANISM: Homo sapiens

<400> SEQUENCE: 51
cagaggttgg aactctgggg c                                                 21

<210> SEQ ID NO 52
<211> LENGTH: 21
<212> TYPE: DNA
<213> ORGANISM: Homo sapiens

<400> SEQUENCE: 52
gataatcttg atatttgggg c                                                 21

<210> SEQ ID NO 53
<211> LENGTH: 18
<212> TYPE: DNA
<213> ORGANISM: Homo sapiens

<400> SEQUENCE: 53
tccattgact actggggc                                                     18

<210> SEQ ID NO 54
<211> LENGTH: 21
<212> TYPE: DNA
<213> ORGANISM: Homo sapiens

<400> SEQUENCE: 54 ttacccttg acttctgggg c                                                  21

<210> SEQ ID NO 55
<211> LENGTH: 21
<212> TYPE: DNA
<213> ORGANISM: Homo sapiens
```

```
<400> SEQUENCE: 55
ggtgtttttg atatctgggg c                                              21

<210> SEQ ID NO 56
<211> LENGTH: 33
<212> TYPE: DNA
<213> ORGANISM: Homo sapiens

<400> SEQUENCE: 56
ccttactact actatcacat ggacgtctgg ggc                                 33

<210> SEQ ID NO 57
<211> LENGTH: 15
<212> TYPE: DNA
<213> ORGANISM: Homo sapiens

<400> SEQUENCE: 57
tttgactact ggggc                                                     15

<210> SEQ ID NO 58
<211> LENGTH: 21
<212> TYPE: DNA
<213> ORGANISM: Homo sapiens

<400> SEQUENCE: 58 cgccccttttg accactgggg c                                             21

<210> SEQ ID NO 59
<211> LENGTH: 27
<212> TYPE: DNA
<213> ORGANISM: Homo sapiens

<400> SEQUENCE: 59
gactactaca cgatggactt ctggggc                                        27

<210> SEQ ID NO 60
<211> LENGTH: 15
<212> TYPE: DNA
<213> ORGANISM: Homo sapiens

<400> SEQUENCE: 60
tttaactcct ggggc                                                     15

<210> SEQ ID NO 61
<211> LENGTH: 21
<212> TYPE: DNA
<213> ORGANISM: Homo sapiens

<400> SEQUENCE: 61
tactactttg gctactgggg c                                              21

<210> SEQ ID NO 62
<211> LENGTH: 18
<212> TYPE: DNA
<213> ORGANISM: Homo sapiens

<400> SEQUENCE: 62
tactttgacc tctggggc                                                  18

<210> SEQ ID NO 63
<211> LENGTH: 21
<212> TYPE: DNA
```

```
<213> ORGANISM: Homo sapiens

<400> SEQUENCE: 63
tactactttg gctactgggg c                                              21

<210> SEQ ID NO 64
<211> LENGTH: 36
<212> TYPE: DNA
<213> ORGANISM: Homo sapiens

<400> SEQUENCE: 64
aaatactact actaccacca catggacgtc tggggc                              36

<210> SEQ ID NO 65
<211> LENGTH: 18
<212> TYPE: DNA
<213> ORGANISM: Homo sapiens

<400> SEQUENCE: 65
cgatcggacg tctggggc                                                  18

<210> SEQ ID NO 66
<211> LENGTH: 153
<212> TYPE: DNA
<213> ORGANISM: Artificial Sequence
<220> FEATURE:
<223> OTHER INFORMATION: Description of Artificial Sequence: primer

<400> SEQUENCE: 66
gtctcaggta ttagttggaa tagtggtagc ataggctatg cggactctgt gaagggccga    60
ttcaccatct caagagacaa cgccaagaac tccctgtatc tgcaaatgaa cagtctgaga   120
gctgaggaca cggccttgta ttactgtgca aaa                                153

<210> SEQ ID NO 67
<211> LENGTH: 153
<212> TYPE: DNA
<213> ORGANISM: Artificial Sequence
<220> FEATURE:
<223> OTHER INFORMATION: Description of Artificial Sequence: primer

<400> SEQUENCE: 67
gtctcaggta ttacgtggaa tagggcagt ctaggatatg tggactctgt caggggccga     60
ttcaccatct ccaaagacag cgtgaagaag ttcctgtatc tgcaaatgaa cagtctgaga   120
actgaggaca cggccttgta ttattgtgta aag                                153

<210> SEQ ID NO 68
<211> LENGTH: 153
<212> TYPE: DNA
<213> ORGANISM: Artificial Sequence
<220> FEATURE:
<223> OTHER INFORMATION: Description of Artificial Sequence: primer

<400> SEQUENCE: 68
gtctcaggta ttacgtggaa tagggcagt ctaggatatg tggactctgt caggggccga     60
ttcaccatct ccaaagacag cgtgaacaag ttcctgtatc tgcaaatgaa cagtctgaga   120
actgaggaca cggccttgta ttattgtgta aag                                153

<210> SEQ ID NO 69
<211> LENGTH: 153
<212> TYPE: DNA
<213> ORGANISM: Artificial Sequence
```

```
<220> FEATURE:
<223> OTHER INFORMATION: Description of Artificial Sequence: primer

<400> SEQUENCE: 69
gtctcaggta ttacgtggaa tagggcagt ctaggatatg tggactctgt caggggccga     60
ttcaccatct ccaaagacag cgtgaagaag ttcctgtatc tgcaaatgaa cagtctgaga   120
actgaggaca cggccttgta ttattgtgta aag                                153

<210> SEQ ID NO 70
<211> LENGTH: 153
<212> TYPE: DNA
<213> ORGANISM: Artificial Sequence
<220> FEATURE:
<223> OTHER INFORMATION: Description of Artificial Sequence: primer

<400> SEQUENCE: 70
gtctcaggta ttacgtggaa tagggcagt ctaggatatg tggactctgt caggggccga     60
ttcaccatct ccaaagacag ctgtaagaag ttcctgtatc tgcaaatgaa cagtctgaga   120
actgaggaca cggccttgta ttatttgtta aag                                153

<210> SEQ ID NO 71
<211> LENGTH: 184
<212> TYPE: DNA
<213> ORGANISM: Artificial Sequence
<220> FEATURE:
<223> OTHER INFORMATION: Description of Artificial Sequence: consensus
      sequence

<400> SEQUENCE: 71
gtctcaagta ttacgtggaa tagggcagt ctaggatatg tggactctgt caggggccga     60
ttcaccatct ccaaagacag cgtgaagaag ttcctgtatc tgcaaatgaa cagtctgaga   120
actgaggaca cggccttgta ttattgtgta aaggccgaga tggctacaac ttcgaaggac   180
aaca                                                                184

<210> SEQ ID NO 72
<211> LENGTH: 179
<212> TYPE: DNA
<213> ORGANISM: Artificial Sequence
<220> FEATURE:
<223> OTHER INFORMATION: Description of Artificial Sequence: consensus
      sequence

<400> SEQUENCE: 72
gtctcaagta ttacgtggaa tagggcagt ctaggatatg tggactctgt caggggccga     60
ttcaccatct ccaagacagc gtgaagaagt tcctgtatct gcaaatgaac agtctgagaa   120
ctgaggacac ggccttgtat tattgtgtaa aggccgagat ggctacaact tcgaaggac    179

<210> SEQ ID NO 73
<211> LENGTH: 161
<212> TYPE: DNA
<213> ORGANISM: Artificial Sequence
<220> FEATURE:
<223> OTHER INFORMATION: Description of Artificial Sequence: primer

<400> SEQUENCE: 73
gtcaccgtct cctcaggtgg atcccgtacc tggggccaag ggactggtca cggatcccgt    60
aaccttatga attcggaaag ggcctggagt gggtctcaag tattacgtgg aatagggca   120 gtctaggata tgtggactct gtcaggggcc gattcaccat c                       161
```

```
<210> SEQ ID NO 74
<211> LENGTH: 187
<212> TYPE: DNA
<213> ORGANISM: Artificial Sequence
<220> FEATURE:
<223> OTHER INFORMATION: Description of Artificial Sequence: primer

<400> SEQUENCE: 74
tcaccgtcct acgaagtcgg ataccgtctg gagtggccac cgtctcgtca ggtatatccc      60
gaactggggc aatggcacct ggtcacggat cggttatgaa ttcggaatgg gcctggagtt     120
gtctcgtatt cctgaacgtg gttcccgtcc ccttatgaat tcggaaaggg cctggagtgg     180
tcaccgt                                                               187

<210> SEQ ID NO 75
<211> LENGTH: 121
<212> TYPE: DNA
<213> ORGANISM: Artificial Sequence
<220> FEATURE:
<223> OTHER INFORMATION: Description of Artificial Sequence: consensus
      sequence

<400> SEQUENCE: 75
tggaataggg gcagtctagg atatgtggac tctgtcaggg gccgattcac catctccaaa      60
gacagcgtga agaagttcct gtatctgcaa atgaacagtc tgagaactca ggacacggcc     120
t                                                                     121

<210> SEQ ID NO 76
<211> LENGTH: 186
<212> TYPE: DNA
<213> ORGANISM: Artificial Sequence
<220> FEATURE:
<223> OTHER INFORMATION: Description of Artificial Sequence: primer

<400> SEQUENCE: 76
cttgggactt ctacgacaat ggcgaaacct tcaacaatcc gtcctcacgg gtggtcgagt      60
caccgtgtcc ctagacacat ctcagaatta tttgtccctg gaagtagtct ctgtgaacgc     120
cgcagacacg ggtatttatt actgtgcggg tggcaccacg tcctcccagg gtcagaggtt     180
ggaatc                                                                186
```

METHODS FOR DETECTION OF REARRANGED DNA

RELATED APPLICATION

This application is the National Stage of International application No. PCT/US97/09534, which claims priority under 35 U.S.C. §119(e) to U.S. Provisional Application Serial No. 60/019,106, filed on Jun. 3, 1996, which is incorporated herein by reference.

BACKGROUND OF THE INVENTION

1. Field of Invention

The invention relates generally to a method for the detection of malignant cells, and the use of the method to monitor disease progression and response to treatment in cancer patients. In particular, the invention relates to the identification of malignant lymphocytes by PCR amplification of immunoglobulin or T cell receptor genes which are uniquely rearranged in the malignant clone.

2. Description of the Related Art

Lymphoid malignancies are characterized by the proliferation of cells which carry a unique genetic marker by virtue of their rearranged receptor genes, the immunoglobulin (Ig) genes in B cells, and the T cell receptor (TCR) genes in T cells. It is well known in the art that germ line genes for both Ig and TCR exist as pools of gene segments which become assembled during the normal differentiation of B and T lymphocytes by a process of site specific recombination (Alberts et. al., 1995). Diversity of Ig and TCR are generated by the combinatorial association of these gene segments from the different pools, so that the total repertoire of antigen receptors is log-folds greater than the actual number of receptor gene segments.

The Ig genes comprise 3 clusters of genes, on three different chromosomes: (1) the heavy chain (IgH) genes, which include the immunoglobulin heavy chains, (2) k light chain genes and (3) l light chain genes, which encode the immunoglobulin light chains. The IgH cluster consists of four pools of gene segments, known as C (constant), J (joining), D (diversity) and V (variable). There are nine C gene segments, arranged in an ordered cluster, which determine the class of the heavy chain. The variable region of the IgH is encoded by pools comprising 6 J segments, 10 or more D segments and at least 50 V segments. The arrangement of these gene segments on the chromosome is depicted in FIG. 1. The Ig light chain genes consist of C, J, and V, but no D segment. Similarly, the genes for the a and b and the g and d chains of the TCR exist on separate chromosomes as pools of C, J, D, and V gene segments.

During differentiation of a T or B cell, the germ line genes are rearranged so that one member of each pool of variable region gene segments (J, D, and V) is randomly selected and the selected segments are joined together. The process of site specific recombination that takes place during lymphocyte differentiation is distinctive, in that during the joining of the Ig and TCR gene segments J, D and V, a variable number of nucleotides may be lost from the ends of the recombining gene segments. In the case of IgH recombination only, one or more nucleotides may also be randomly inserted at the joining site. This loss and gain of nucleotides at the joining sites Ig or TCR is a source of further diversity. It yields rearranged Ig or TCR genes which may be different in length. If short regions spanning the junctions of gene segments (VD, DJ, and JC) are examined, they may be substantially different in length.

The variable regions of both Ig and TCR comprise three regions with little sequence homology between different clones, which are known as "hypervariable" or "complementarity-determining regions" (known as CDR1, CDR2, and CDR3, shown in FIG. 1). The intervening portions of the variable region are more consistent between different clones, and are known as "framework" (FR1, FR2, FR3, and FR4). The CDR3 region, which is encoded by the VJ junctional region of the light chain, and the D region plus the VD and DJ junctional regions of the heavy chain, is the most highly variable, due to the somatic mutations introduced during recombination, as described above.

Each B lymphocyte expresses only a single rearranged IgH gene, and a single rearranged k or l gene. Each mature T lymphocyte expresses a single TCR a chain and a single TCR b chain. In a lymphoid malignancy, if clonal expansion of a tumor progenitor cell took place after rearrangement of the Ig or TCR gene, it is possible to identify a signature or clonotypic rearrangement which is characteristic of the malignant clone. With the appropriate molecular probes, cells related to the malignant clone can be distinguished from cells with unrearranged Ig or TCR genes, or cells which carry different rearrangements. The rearrangement of Ig or TCR genes in a clone is called its "clonotypic rearrangement".

It is clinically important to be able to detect and characterize tumor cells, not only at diagnosis, but during and after treatment. It is also important to be able to detect any malignant cells that might contaminate a population of stem cells destined for autologous transplantation after ablative chemotherapy. The following methods which are currently available to detect malignant cells carrying a monoclonal or clonotypic rearrangement in patient samples differ in their accuracy and their sensitivity. None are quantitative.

Morphological examination of cells in patient blood samples or biopsies is currently used, but is relatively insensitive in detecting minimal residual disease. Also, cells which might be related to the malignant clone, but are at a different stage of maturation, and thus have a different morphology from the bulk of the tumor cells, are probably missed.

Southern blot hybridization analysis of isolated DNA, a technique which is well known in the art, requires that between 1 and 5 percent of the cells in the patient sample carry a clonotypic rearrangement for it to be detected. Although this technique has been used to detect a monoclonal population of cells which are present in high frequency, it is not useful for the detection of minimal residual disease, because it is not sensitive enough. Also, it cannot provide sequence information that definitively characterizes a malignant clone.

Recently, techniques have been developed which rely upon the use of the polymerase chain reaction (PCR) to amplify clonotypic DNA rearrangements in malignant cells. PCR, which is well known in the art (U.S. Pat. No. 4,683, 202 to Mullis, 1987), is a process of repeated cycles of DNA denaturation, followed by DNA synthesis which is used to amplify segments of DNA between two fixed anchor points on a DNA molecule.

Single stranded oligonucleotide primers, called PCR primers, are constructed (based on previously obtained nucleic acid sequence information) which will hybridize to the anchor points, one primer, the upstream primer, on the sense strand, and the other primer, the downstream primer, on the antisense strand. The DNA segment is heat denatured, and then cooled to a temperature at which the PCR primers will anneal to their complementary sequences on the DNA segment. A heat-stable DNA polymerase enzyme then copies the DNA between the two anchor points. In 20-40 or more successive cycles of denaturation and DNA synthesis, the DNA segment of interest (between the two anchor points) can be amplified a million-fold or more. The two anchor points must be within a few thousand nucleotides of each other for efficient amplification to occur. In RT-PCR (reverse transcriptase PCR), the RNA in cells is used as the template. It is first copied into cDNA using the enzyme reverse transcriptase, and the resultant cDNA is subjected to the PCR reaction.

In the context of clonotypic rearrangements, "consensus" or "framework" PCR primers which hybridize to DNA in the constant or framework regions of rearranged Ig or TCR are used to amplify DNA prepared from patient blood or bone marrow samples containing a high proportion of tumor cells. For example, the upstream primer might be chosen from the 5' end of the V segment, and the downstream primer from the J segment. Germ line (unrearranged) DNA will not be amplified to detectable levels because the distance between the primers is too great for efficient synthesis. A monoclonal rearrangement can often (but not always) be detected as a single band if the amplified DNA is electrophoresed on an appropriate gel. This amplified DNA represents the putative hypervariable region containing the clonotypic V(D)J rearrangement. More specific PCR primers, referred to as patient-specific PCR primers can be designed once the clonotypic sequence has been determined. The following prior art utilizes PCR technology.

U.S. Pat. No. 5,418,132 to Morley (1995) teaches a method for the diagnosis of leukemia and lymphoma by PCR amplification of Ig or TCR gene segments using consensus framework primers, followed by separation of the PCR products on the basis of size. Because rearranged Ig or TCR genes vary somewhat in their size, as noted above, a clonotypic rearrangement that has been amplified can often be detectable as a discrete band on a gel. If the patient sample does not contain a monoclonal population of cells, size separation will yield a smear, with no detectable discrete band. However, the inventors disclose that this method fails to produce a discrete band with every patient sample, even when multiple pairs of primers are employed. This method could be useful during initial diagnosis when the tumor burden is high, but is not proposed as a means of following minimal residual disease after treatment, because it does not involve detection of a specific clonotypic rearrangement.

Flow cytometry-based fluorescent in situ hybridization (FISH) using immunoglobulin heavy chain variable region probes (Cao et al., 1995a; 1995b) has been suggested as a method to detect clonotypic rearrangements in individual cells in myeloma. The FISH technique involves hybridization of a biotin-labeled anti-sense RNA probe to the unamplified RNA in fixed cells in suspension. Cells which contain RNA complementary to the clonotypic sequence are then detected by means of flow cytometry. The sequence of the anti-sense RNA probes are derived by amplifying the mRNA expressed in myeloma patients' bone marrow mononuclear cells using RT-PCR from homogenized total RNA with consensus framework PCR primers for the IgH variable region. Because the RNA in the cells to be assayed is not amplified, this method is only sensitive enough to detect cells in which the clonotypic RNA is highly abundant, but it cannot detect cells with a low level of the RNA, or cells in which the DNA is rearranged, but is not being transcribed. For example, FISH might work well with myeloma plasma cells, which are virtual "immunoglobulin factories", and contain extremely high concentrations of mRNA encoding the Ig being produced by the cell. However, FISH would not be sensitive enough to detect pre-B cells or B cells which share the clonotypic rearrangement of a myeloma malignant clone, but do not transcribe or have a low level transcription of the gene.

RT-PCR or PCR using patient-specific PCR probes have been used to amplify bulk RNA or DNA preparations made from myeloma patient samples in an attempt to follow minimal residual disease (Billadeau et. al 1991; Billadeau et al, 1992; Billadeau et al., 1993; Chen and Epstein 1996; Cao et al. 1995). In all of these reports, the sequences of the PCR primers were originally derived from amplification of bulk RNA or DNA isolated from tumor-containing material, which the present inventors find may amplify a sequence which is unrelated to the malignant clone. Another major problem with this approach is that the use of bulk nucleic acid to detect clonotypic sequence does not give quantitative results, and may grossly underestimate the frequency of clonotypic sequences.

A reliable method to quantitate malignant cells during assessment of minimal residual disease does not currently exist. A reference by Yameda et al., 1990 proposed a method based on cloning the products of a PCR amplification into bacteriophage and attempting an analysis of the ratio of phage carrying the clonotypic sequence to phage carrying any other rearrangement. Billadeau et al. (1991) proposed to quantitate a PCR amplification of bulk nucleic acid by preparing a standard curve by seeding known numbers of clonotypic cells into a population of non-rearranged cells. Both proposed methods are very indirect. The FISH method of Cao, cited above, while it provides an analysis on a single cell level, is too insensitive to be quantitative, measuring only the cells which express very high levels of mRNA.

In situ PCR and in situ RT-PCR are known in the art as means to detect nucleic acid sequences in single cells (U.S. Pat. No. 5,436,144 to Stewart and Timm, 1995; Nuovo, 1994).

It is clinically important to be able to monitor the members of a malignant T or B lymphocyte clone, over time in order to determine the effect of treatment on cells of malignant lymphocyte clones. Since most of these malignancies are heterogeneous in differentiation state and/or morphology, the only marker that unequivocally confirms a relationship with the malignancy is the immunoglobulin rearrangement of the IgH, light chain (k or l) or the T cell receptor a, b, g or d. Assays using bulk nucleic acid from lymphocyte populations are not quantitative and do not identify the clonotypic cell types present in blood, lymphoid tissue or bone marrow. Often the malignant lymphocyte comprising the major cellular mass of primary tumor divide slowly or not at all, and may be terminally differentiated with little generative capacity. Hematopoietic malignancies appear to be hierarchical with components at sequential states of differentiation not easily detected with conventional clinical assays, especially if they are present at low frequency. Thus at present, the effects of treatment on the full hierarchy of malignant cells in diseases much as myeloma, lymphoma and chronic and acute lymphocytic leukemias, cannot be assessed.

DESCRIPTION OF THE DRAWINGS

FIG. 3 is a sequence alignment of CDR2 and CDR3 sequences obtained from sorted blood B cells and autologous BM plasma cells. IgH bands amplified in hemi-nested PCR, shown in FIG. 2, were cut out, ligated into a sequencing vector, and sequenced using dideoxy chain termination. (A) shows the CDR3 sequence obtained for 2 of the 10 sorted BM plasma cells (from FIGS. 2 and 3 others from the JOD-5 BM sample: in total, the product from 11 individual BM plasma cells was sequenced). Sequences were compared to known sequences using BLAST and the VBASE database, and aligned using GCG software. All 10 sequences were most closely related to the DP-31 VH3 gene family. The DP-31 sequence (line 1, SEQ ID NO.66) aligned with 2 representative JOD B cells (lines 2 and 3, SEQ ID NOS.67 and 68 respectively) and 2 representative BM plasma cells (lines 4 and 5, SEQ ID NOS.69 and 70 respectively), as well as the consensus JOD sequence from the 10 plasma cell sequences (line 6, SEQ ID NO.71). Although the JOD sequence varies from the P-31 sequence in several places, the same variation occurred in all JOD B and plasma cells, with few exceptions (e.g. BM plasma cell 4.4, line 5, positions 213, 214, 215). CDR2 and CDR3 sequences used for primers in PSA are underlined. (B) shows the JOD consensus sequence (line 1, SEQ ID NO.72) aligned with the unrelated BM plasma cell 5.3 (line 2, SEQ ID NO.73) and with the unrelated B cell (line 3, SEQ ID NO.74), as well as a related BM plasma cell for comparison (line 4). The unrelated B cell sequence aligned with VH4a, and the unrelated plasma cell sequence aligned best, although at only moderate homology, with the DP-31 sequence. The absence of bands from water controls (FIG. 2) and the amplification of an unrelated IgH sequence from plasma cell #11, shows that the presence of a common sequence for 10/11 cells amplifying a band, does not reflect contamination by JOD DNA, and that amplification requires the presence of a cell in the tube. The consensus rearrangement identified in 10/11 plasma cells was designated as clonotypic for JOD.

SUMMARY OF THE INVENTION

Figure 1:
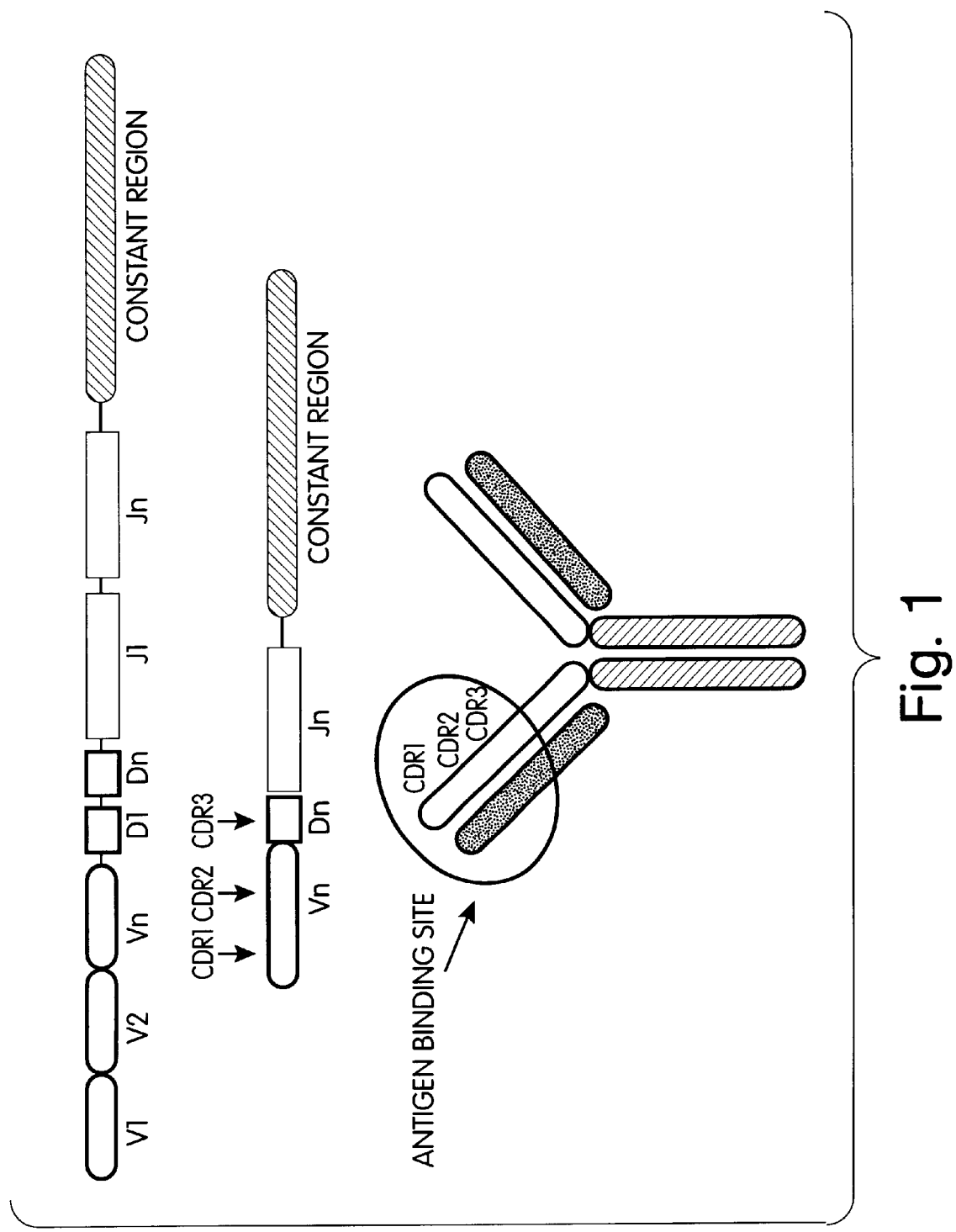
FIG. 1 is a schematic drawing of the immunoglobulin heavy chain locus in germ line and rearranged DNA.

Recognizing the need for a clinically feasible test for assessing minimal residual disease in lymphoid malignancies which would require a more accurate, sensitive and quantitative method to detect clonotypic rearrangements in patient samples than was currently available, the object of the invention was to develop a method with the following features: consistently accurate PCR primer specificity, a quantitative readout, and high sensitivity. Ideally, the method should also be compatible with allowing qualitative identification of the cell types which express a given clonotypic rearrangement.

The invention is based upon the discovery that the most accurate and quantitative information regarding the identity of a clonotypic sequence and frequency of clonotypic cells in patient samples is obtained from RT-PCR or PCR analysis of nucleic acid in whole cell lysates, rather than from purified bulk preparations of nucleic acid. The inventors made the following observations:

PCR amplification of bulk nucleic acid preparations from MM plasma tumour cells using consensus primers for the VDJ region frequently yields a sequence which turns out not to be the clonotypic sequence of the malignancy.

Quantitative measurements of the frequency of a clonotypic sequence made on bulk nucleic acid preparations tend to grossly underestimate the frequency of such cells.

The inventors have circumvented these problems, which hinder the development of a clinical test for minimal residual disease:

(1) by performing RT-PCR or PCR directly in cell lysates made within a few hours of being harvested from the patient. In the case of MM patient samples, PBMC or BMC are diluted in a small volume (several microliters) of an appropriate lyses buffer. RT-PCR or PCR is performed directly in the cell lysate; and (2) by performing RT-PCR in situ in intact cells. In situ RT-PCR amplification is carried out using patient specific VDJ region primers in cells affixed to slides, which allows for the direct visualization and counting of clonotypic cells.

In accordance with the invention a method for the detection of clonotypic gene rearrangements in patient cell samples comprises two phases. In the first phase, the nucleotide sequence of the clonotypic rearrangement is determined, and the patient-specific PCR probes are designed, using the following steps:

(a) isolating single cells or pools of up to 1000 cells by means of cell sorting, limiting dilution, or other means from a tumor cell-rich sample of patient cells, (b) amplifying a region of DNA comprising at least a portion of VDJ in several of the isolated single cells or pools o f up to 1000 cells by PCR or RT-PCR, using pairs of consensus framework primers which are known to amplify DNA in the variable region of Ig or TCR, or alternatively, amplifying DNA known to contain another type of DNA rearrangement, such as a chromosomal translocation using appropriate conservative primers;

(c) determining the nucleotide sequence of the amplified DNA segments;

(d) constructing patient-specific PCR primers, which bracket the amplified nucleotide sequence, specific for the CDR, CDR2, and/or the CDR3 regions, or the CDR1, CDR2, or CDR3 region, or any set of primers that specifically amplify the unique hypervariable regions of the IgH, k or 1 immunoglobulin gene, or the TCR a, b, g or d chain, or any set of primers that specifically amplify a clonotypic rearrangement in lymphoid malignancies.

(e) confirming that the patient-specific primers amplify the sequence obtained in (c) above, and no other sequences.

The second phase of the method of patient specific amplification comprises the use of in situ RT-PCR or PCR to amplify a nucleotide sequence comprising a clonotypic rearrangement in intact cells, without removing the DNA or RNA from the cell, as follows:

(a) performing in situ PCR or in situ RT-PCR, using the said patient-specific probes on patient tissue samples comprising fractionated or unfractionated white blood cells, peripheral blood mononuclear cells, or bone marrow cells, or any other patient samples such as tissue biopsies, which are either fixed to slides, or fixed in solution.

(b) directly detecting the resultant amplified DNA in cells, or, for an additional confirmation of specificity, hybridizing the amplified DNA in situ to labeled nucleic acid probes comprising an internal portion (which excludes any primer sequence) of the clonotypic region.

An alternative or complement to the second phase of the method described above comprises determining the frequency of clonotypic cells by means of a limiting dilution RT-PCR or PCR assay as follows:

(a) diluting cells in series to give from approximately 1000 cells to 1 cell per tube, (b) lysing the cells in the tubes, (c) performing RT-PCR or PCR on the resulting material, (d) counting the number of tubes containing the clonotypic sequence for each dilution, and (e) estimating the frequency of clonotypic cells.

The advantage of the limiting dilution methodology is that a clonotypic sequence can be detected from a single cell as in the in situ assay, but the limiting dilution method is simpler and more cost effective. Cells destined for this method can be processed quickly and stored at −80° C. for later analysis. Cells destined for in situ RT-PCR must be fixed, washed and applied to slides within 18–24 h.

The invention extends to a patient-specific kit designed for the analysis of clonotypic cells in patient samples comprising at least one but preferably two patient-specific PCR primers, and a nucleic acid probe comprising at least a portion of the clonotypic V(D)J region which is amplified by the patient-specific PCR primers or the patient-specific primer and an appropriate consensus primer.

The method is used to detect malignant lymphocytes in patient samples in a wide variety of applications, which include, but are not limited to the following:

to monitor clonotypic cells before during and after treatment in any lymphoid malignancy in which any Ig or any TCR genes are rearranged, including, but not limited to multiple myeloma, Hodgkin's lymphoma, and ALL;

to monitor clonotypic cells before, during or after treatment in lymphoid malignancies in which the clonotypic rearrangement comprises a chromosomal translocation;

to monitor the presence of clonotypic cells in a population of cells to be transplanted, for example bone marrow cells or isolated stem cells;

to monitor the presence of clonotypic cells in premalignant conditions such as monoclonal gammopathy of undetermined significance, indolent myeloma, or smoldering myeloma;

to monitor the presence of clonotypic cells in autoimmune diseases characterized by autoimmune clonal expansion;

for use in the identification of the variety of cell types representing the various differentiation stages which comprise a malignant clone; and for use in the development of treatment protocols which require sensitive tests for malignant cells in blood, bone marrow and other tissues.

Broadly speaking, one aspect of the invention is a method for determining the correct patient-specific clonotypic nucleic acid sequence for a tumour comprising:

performing RT-PCR or PCR with consensus primers using the unpurified nucleic acid released from small numbers of lysed tumour cells, and preferably a single tumour cell, as a template, to generate a product, and obtaining the nucleotide sequence of the product.

Another aspect of the invention is a method for analyzing the number of cells in a population of cells which contain a clonotypic sequence, comprising:

performing RT-PCR or PCR with at least one correct patient specific clonotypic primer to amplify the clonotypic nucleotide sequence in intact cells, and detecting the amplified clonotypic sequence in the intact cells.

A further aspect of the invention is a method for analyzing the number of cells in a population of cells which contain a clonotypic sequence comprising:

performing RT-PCR or PCR with at least one correct patient specific clonotypic primer to amplify the clonotypic nucleotide sequence using the unpurified nucleic acid released from cells which have been subjected to limiting dilution and lysed, and detecting the amplified clonotypic sequence.

DETAILED DESCRIPTION OF THE INVENTION

The invention comprises methods for the detection of clonotypic DNA rearrangements in lymphoid tissues. The inventors encountered two problems during their investigation of the role of blood-borne clonotypic B cells in myeloma. The first was that no existing method of screening for clonotypic rearrangements was both sensitive enough and quantitative enough to provide a reliable count all of the clonotypic cells in all states of differentiation. The second was that in attempting to generate patient-specific PCR primers using bulk RNA or DNA isolated from myeloma bone marrow cells, it became evident that consensus primers to the IgH variable region sometimes amplify a VDJ sequence which is not the clonotypic rearrangement present in the myeloma cells. The reason for this was not clear. However, use of the wrong PCR primers is fatal to any attempt to assay for clonotypic cells in patient samples.

Identification of Clonotypic Sequence, Design and Testing of Patient-specific Primers One aspect of the invention provides for a reliable method to generate PCR primers for use in screening. This aspect of the invention is based on the premise that in order to unequivocally determine the rearranged Ig or TCR sequence of a malignant clone, it is necessary to amplify this rearrangement from a small number of cells, preferably individual cells, sequence the amplified product, and then confirm that the majority of cells thought to be malignant actually express the identified sequence. This aspect of the invention comprises the following steps:

(a) performing PCR using consensus framework primers on a number of single tumor cells or groups of 1000 or fewer tumor cells to amplify the clonotypic rearrangement, (b) obtaining the amplified PCR products by gel electrophoresis, (c) obtaining the nucleotide sequence of the amplified PCR products from several tumor cells before assigning a sequence to the malignant clonotypic rearrangement, (d) preparing patient specific DNA primers based on the clonotypic sequence, (e) testing the patient-specific primers, once constructed, for their ability to amplify the clonotypic sequence and only the clonotypic sequence in patient samples.

This aspect of the invention is directed toward overcoming the problem that use of homogenized nucleic acid as the initial source of the sequence can amplify an infrequent and thus inaccurate sequence. It therefore provides for the identification of the clonotypic rearrangement, using single tumor cells, or very few tumor cells, rather than bulk homogenized DNA. For this procedure, it is desirable to obtain a tumor-rich sample of cells, or to enrich the cell sample for tumor cells, if possible. For multiple myeloma, bone marrow plasma cells are an ideal source of tumor material. Single cells can be sorted using a cell sorter such as the ELITE Autoclone (Coulter Electronics), using surface markers (which are detectable by fluorescently labeled antibodies), and/or size gating to distinguish tumor cells from non-tumor cells in the patient samples. For example, a large size, and a high concentration of both the CD38 marker (detectable by an antibody to CD38) and immunoglobulin (detectable by an antibody to immunoglobulin) are diagnostic for myeloma plasma cells, as detailed in the Materials and Methods section below. If the patient cell sample contains primarily tumor cells, the single cells can be plated by limiting dilution, without the need for cell sorting.

The single cells, prepared as indicated above, are placed into a small volume consisting of a few microliters of an appropriate lysis buffer, depending on whether RNA (RT-PCR) or DNA (PCR) will be used as the starting material for amplification (see Materials and Methods). In all cases control samples which do not contain a cell are included. At this point it is possible to amplify DNA (which is present in only one copy) in the single cell, or to copy RNA (which may be present in hundreds of copies, or none at all, depending on the cell type) into cDNA which is then amplified. In cells such as myeloma plasma cells, RNA is relatively abundant, making RT-PCR practical. However, RNA is much more labile than DNA, so cell samples which are not optimally fresh, in which RNA may be degraded, could still be used for PCR, rather than RT-PCR. If RT-PCR is done, then RNA is copied into cDNA by means of the enzyme known as reverse transcriptase, using methodology well known in the art. The methodology used by the inventors for this step is outlined in the Materials and Methods.

PCR is then carried out in order to amplify all sequences with VDJ rearrangements. The appropriate consensus framework primers are chosen based upon known sequences in the constant or framework regions of the Ig or TCR gene which bracket the VDJ recombination sites, or a chosen hypervariable sequence. For Ig, the rearranged heavy chain has more diversity than the rearranged light chain, so that it is a better choice as a probe for clonotypic sequence. However, if the heavy chain is not rearranged in the tumor being assayed, primers to the light chains can be used.

In order to minimize spurious amplification products, the inventors in a preferred embodiment carried out two rounds of PCR using hemi-nested consensus framework primers specific for IgH, the sequences of which are given in Table 1, (SEQ ID NOS.5–7). The first round of amplification was done with an upstream primer which hybridizes in the FR2 region (FR2, SEQ ID NO.5), and a downstream primer which hybridizes in the J region (JH1, SEQ ID NO.6). An aliquot of the material from the first round of amplification was used for a second round of amplification using the same upstream primer, and a downstream primer (JH2, SEQ ID NO.7) which hybridizes in the J region, just upstream (on the 5' side) of the JH1 primer.

The products of the second round of amplification are subjected to electrophoresis in an agarose or polyacrylamide gel, using methodology which is well known in the art, including the use of appropriate size markers. The PCR products are variable in length, depending on the choice of primers and length of the DNA segment which is bracketed by the primers. However, most products will be within the range of 150–200 nucleotides. The bands are cut out of the gel, separated from the gel material using methodology well known in the art, ligated into a sequencing vector and sequenced using standard methodology (see Materials and Methods). The sequences obtained for the panel of single cells can be conveniently compared to known Ig, TCR or other sequences using information contained in data bases such as BLAST and the VBASE database, and can be aligned using appropriate software. Generally, the sequence obtained aligns with one of the VH families if IgH PCR primers have been used. Once the sequences of a number of cells are obtained and aligned, it is then possible to assign a consensus sequence to the clonotypic rearrangement. FIG. 3A exemplifies the alignment of sequences, and the consensus sequence assigned in a preferred embodiment. The experience of the inventors in using single purified myeloma plasma cells as starting material is that many of the sequences obtained are identical or nearly identical. However, the number of sequences obtained which are clearly unrelated to the malignant clone will vary with the purity of the tumor cell starting material.

Once the clonotypic sequence is known, it is possible to design patient-specific PCR primers specific for one or more of the most variable regions in the sequence. In a preferred embodiment, the inventors chose the upstream primer in the CDR2 region and the downstream primer in the CDR3 region of the rearranged IgH.

The next step is to confirm that the primers are truly specific, in that they amplify the clonotypic sequence that they bracket, and only that sequence. Single cells from the tumor cell-rich source are again used as starting material for PCR or RT-PCR. Appropriate controls, such as unrelated single B cells or T cells are also included in the experiment. The first round of amplification is carried out using the consensus primers (in the preferred embodiment, the FR2 and the JH1 primers). However, the second round of amplification is performed using the patient-specific primers. Products are run on a gel and sequenced as above. If the primers amplify the correct product—the clonotypic sequence in tumor cells, but do not amplify any product in irrelevant cells, then they have been vetted as patient-specific primers suitable for use in analytical patient-specific amplification (PSA), to be described below. If the primers do not amplify a product, or if they amplify a spurious product, other primers based on the clonotypic sequence can be selected.

Analysis of Clonotypic Cells Using PSA in Single Cells

In order for a screening test to be useful clinically for the purpose of following the progress of disease and treatment, and in order for clinical decisions to be based upon the results of the test, it must have both a quantitative readout (the assay must be done at the level of single cells, rather than bulk preparations of nucleic acid made from a whole population of cells), and sensitivity (the RNA or DNA reflecting the clonotypic rearrangement in the single cells must be amplified to detectable levels, so that clonotypic cells expressing low levels of RNA or no RNA can be detected).

A further aspect of the invention therefore provides for the use of in situ PCR or RT-PCR with patient-specific PCR primers, which may be produced as indicated above, to detect clonotypic rearrangements in single cells. In a preferred embodiment, a novel use for in situ RT-PCR is described for amplifying the CDR1-CDR2-CDR3 regions of individual cells placed on a slide, or suspended in a solution. A cell with at least one gene copy of the patient-specific rearrangement is amplified and is visualized using an appropriate means, which may be colorimetry or autoradiography if the process is carried out on slides, or fluorescence if the assay is carried out in suspension.

The patient samples to be analyzed can include unpurified white cells from blood after red cell lysis (WBC), isolated peripheral blood mononuclear cells (PBMC), or bone marrow mononuclear cells (BMMC). Any of these cell populations can be subjected to further fractionation, selection or depletion using standard methods such as FACS sorting. For example, to quantitate the proportion of T cells with a specific clonotypic rearrangement, one approach would be to positively select for T cells using an antibody to a T cell marker such as CD3 using a cell sorter, and to examine the selected T cells for the presence of the clonotypic rearrangement. Cells are generally formalin fixed before sorting and purification in order to preserve RNA. If sorted cells are to be used, approximately 10,000 cells (using an ELITE Autoclone (Coulter) or comparable equipment) sorted into microtitre wells are sufficient. The method is also amenable to using tissue biopsies or sections from solid organs such as spleen and lymph node.

For analysis on slides, the cells can be placed onto appropriately treated siliconized glass slides (for example, In situ PCR glass slides from Perkin Elmer) in three spots each, to accommodate processing of positive and negative controls on the same slide. RT-PCR is carried out essentially according to published methods (Nuovo, 1994), after fine-tuning the system for the particular cell types and PCR primers being used. The conditions for PCR and RT-PCR which gave optimal results for the primers used in the Examples are detailed in the Materials and Methods.

Another aspect of the invention encompasses, as an alternative to amplification of clonotypic rearrangements in cells affixed to slides, performing the in situ PCR or in situ RT-PCR in cells in suspension, using methods generally disclosed in U.S. Pat. No. 5,436,144 to Stewart and Timm (1995). Detection of clonotypic cells is accomplished by means of flow cytometry. For example, the PCR amplification step can be carried out in the presence of a biotinylated dNTP, which can be detected in flow cytometry using fluoresceinated (FITC-labeled) or phycoerytherin-labeled avidin. Using this methodology, it is feasible to use two-color flow cytometry to detect both the clonotypic DNA marker and a cell surface marker. It is therefore possible to positively and sensitively identify malignant cells which exist at a particular differentiation state, as defined by expression of cell surface markers, such as CD10, CD34, or CD38.

In a further aspect of the invention, the clonotypic specificity of the product of in situ amplification is confirmed by a step comprising hybridization of this product to a nucleic acid probe comprising an internal portion (excluding any primer sequence) of the clonotypic region (for example the IgH V(D)J region). The amplification step is carried out in the absence of labeled dNTPs, so that the PCR product is unlabeled, and detection of cells positive for the clonotypic sequence is done by means of a labeled nucleic acid probe. Alternatively, PCR products could be labeled with a label which will not interfere with detection of the hybridization probe. The process of in situ hybridization, both on cells fixed to slides and in cells in suspension, is well known in the art. The nucleic acid probes consist of a labeled single stranded RNA.

In a further aspect of the Invention, rather than amplifying the clonotypic sequence in situ in intact cells, the cells are subjected to limiting dilution, down to 1 cell per tube, lysed, and RT-PCR or PCR is carried out on the unpurified nucleic acid which has been released from the cells. This method differs from methods used in the prior art in that the released nucleic acid is used without further purification or even ethanol precipitation. The inventors have found that by performing RT-PCR on unmanipulated cell lysates, it is possible to detect clonotypic sequence which is the product of a single cell. The inventors believe that when nucleic acid, especially RNA is purified, material is lost or degraded. This can lead to a gross underestimation of the number of cells within a population which contain clonotypic sequence. The inventors avoid loss and degradation of RNA in cell samples by firstly, placing cells in a buffered solution which inhibits degradation of RNA, and secondly, by not performing any manipulations on the RNA before it is subjected to reverse transcription and PCR.

This aspect of the invention, which is capable of detecting single cells containing clonotypic sequence, provides an alternative to the use of in situ RT-PCR and in situ PCR. It is therefore possible to use this method to determine the frequency of clonotypic cells in a population of MM PBMC, MM BM or other cells. A limiting dilution of cells, followed by patient specific amplification is performed. Defined numbers of PBMC or other cells are placed in PCR tubes in a dilution series to give from approximately 1000 cells to 1 cell per tube as soon as possible after isolation. Controls containing no cells are included. The products of amplification are detected on ethidium bromide stained gels.

Generally, with MM PBMC, all wells containing 1000, 300, 100 and 30 cells contain the clonotypic nucleotide sequence, indicating that at least 3 out of 30 or 10% of cells are clonotypic. If 2 wells containing 1 cell per well are positive, that would indicate that approximately 66% of PBMC are clonotypic. More than 3 replicates can be used to obtain more precise numbers.

The details of this aspect of the invention are outlined in Example 3 below.

The inventors anticipate that this aspect of the invention will allow for testing of patient samples which are obtained in centres which are not equipped to handle in situ RT-PCR or even cell sorting. The inventors envision that a clinical lab would obtain a "sample collection kit" comprising tested reagents and tubes. For example:

PCR microtubes containing 8 ml of lysis buffer (1.2× transcription buffer, a non-ionic detergent and RNASE inhibitor),

PBS, tubes for diluting cells, and instructions.

The instructions would direct the technician to:

process blood or bone marrow on Ficoll to obtain mononuclear cells, which is a standard laboratory procedure;

re-suspend the washed cells to a concentration of one million ($10^6$) cells per ml of PBS;

make dilutions (3 or 10 fold) by diluting the appropriate volume of cell suspension into PBS to generate dilutions down to $10^3$ cells/ml (at that dilution 1 microliter contains 1 cell) (for example, 100 ml of $10^6$ cells/ml into 900 microliters of PBS generates a dilution containing $10^5$ cells/ml, etc.);

transfer 1 microliter from each cell suspension into ice cold PCR tubes containing the lysis buffer in triplicate; and freeze at −80° C., and ship on dry ice to a core lab.

In the core lab, bone marrow cells samples treated as above would be subjected to RT-PCR using consensus primers to determine the clonotypic sequence for the patient according to the method of the invention. Blood, bone marrow or other types of cell samples treated as above would be subjected to RT-PCR using patient specific primers to determine the frequency of clonotypic cells in the samples.

Applications

The methods of the invention can be used for the analysis of any malignancy which carries a clonotypic rearrangement for which it is possible to generate patient-specific PCR primers. These include:

(1) malignancies of the T cell lineage, which carry rearrangements of the genes for the a, b, g or d chains;

(2) malignancies of the B cell lineage, which carry rearrangements of the genes for the immunoglobulin heavy chain, or the k or l light chains, (3) hematological malignancies in which a chromosomal translocation provides a clonotypic marker, many of such translocations involve an Ig or TCR locus (exemplified by, but not limited to, translocations involving chromosome 11 band q23, which occurs frequently in both myeloid and lymphoblastic leukemias (Rowley, 1990), and the translocation of the c-myc protooncogene with the IgH locus (Taub et. al. 1982). Translocations, involving Ig or TCR loci have been identified in stem cell leukemia, T cell-ALL, T cell CLL, Adult T cell Leukemia, T-prolymphocytic leukemia, high and low grade lymphoma, diffuse lymphoma, B cell CLL, multiple myeloma, follicular lymphoma, B-CLL, as well as Burkitt's lymphoma.

The methods of the invention can be used to detect malignant lymphocytes in patient samples for a wide variety of applications:

to monitor clonotypic cells before during and after treatment in any lymphoid malignancy;

to monitor the presence of clonotypic cells in a population of cells to be transplanted, for example bone marrow cells or isolated stem cells; (The failure of treating malignancies such as multiple myeloma with ablative chemotherapy and radiotherapy followed by autologous bone marrow or stem cell transplantation has been attributed in part to contamination of the transplant with cryptic tumor cells.)

to monitor the presence of clonotypic cells in pre-malignant conditions such as monoclonal gammopathy of undetermined significance, indolent myeloma, or smoldering myeloma;

to monitor the presence of clonotypic cells in autoimmune diseases characterized by autoimmune clonal expansion;

for use in the identification and quantitation of the variety of cell types representing the various differentiation stages which comprise a malignant clone; and for use in the development of treatment protocols which require sensitive tests for malignant cells in blood, bone marrow and other tissues.

The invention can be better understood by reference to the following non-limiting examples, which illustrate the use of the methods of the invention to quantitate the number of clonotypic B cells in the blood of multiple myeloma (MM) patients over time, before, during and after chemotherapy.

MM is characterized by the presence of monoclonal immunoglobulin in the blood, lytic bone lesions, and often large numbers of monoclonal plasma cells in the bone marrow. Although many patients respond to treatment, nearly all relapse and become refractory to treatment (Barlogie et al., 1989; Greipp, 1992). While it is clear that monoclonal plasma cells located in the bone marrow directly or indirectly mediate most symptoms of myeloma, these cells do not appear to have the qualities of growth and spread required of a malignant progenitor cell. Consistent with this, the degree of reduction of plasma cell burden (Bergsagel, 1979) or of monoclonal immunoglobulin (Palmer et al., 1989) does not correlate with enhanced survival, and the extent to which bone marrow used for transplantation is contaminated with plasma cells has little impact on patient survival (Barlogie et al., 1989). A number of observations have led to the view that the generative compartment in myeloma includes B lineage cells found in the bone marrow, the blood or both, at a stage of differentiation preceding that of plasma cells (Pilarski and Jensen, 1992; Bergsagel et al. 1995; Pilarski et al, 1996; Jensen et al., 1991; Boccadoro et al, 1983; Hulin et al, 1978; Omede et al, 1993; Caligaris-Cappio et al, 1985; Berenson et al, 1987; Billadau et al., 1993; Takashita et al, 1994). Normal plasma cells are terminally differentiated B cells which do not divide, but which are active in immunoglobulin synthesis. There is no direct evidence that the malignant clonotypic plasma cells in multiple myeloma divide either. However, because there has been no way to detect the generative precursors of multiple myeloma plasma cells, clinical analysis as well as treatment has focussed on the plasma cell. Precursors have thus far been overlooked, although their presence or absence may be crucial to designing successful treatment protocols.

A number of studies have demonstrated cells in blood of myeloma patients with an IgH rearrangement identical to that of autologous bone marrow plasma cells (Bergsagel et al, 1995; Bersenson et al, 1987; Takashita et al, 1994; Bakkus et al, 1994; Billadeau et al, 1992; Corradini et al, 1993; Gazitt et al., 1994; Owen et al., 1994; Sassel et al., 1990; Dreyfus et al., 1993; Mariette et al., 1994; Cirradini et al., 1995; Chen and Epstein, 1996). The differentiation stage of these blood cells and their number has been controversial. A first step towards evaluating the extent to which peripheral blood lymphocytes include malignant myeloma relatives is to quantitate the number of clonotypic B cells in the circulation. Previous work showing the presence in circulating cells of clonotypic rearrangements have provided a wide range of estimates (Billadeau et al., 1992; Dreyfus et al., 1993; Chen and Epstein, 1996; Vescio et al., 1995; Billadeau et al., 1995). All of these estimates are based on the apparent frequency of a given sequence within homogenized DNA or RNA from a heterogeneous population of cells.

The inventors have previously identified a large subset of cells bearing CD19+ (a diagnostic marker for B cells) in the blood of myeloma patients some of which have clonotypic sequences (Bersagel et al., 1995), with the phenotype of late stage B cells and properties consistent with malignant status (Pilarski et al. 1996). In the examples below, the inventors used the methods of the invention to unequivocally determine the clonotypic sequence, and to quantitate the number of clonotypic CD 19+ B cells in the blood of multiple patients.

Materials and Methods

Patients: Blood and bone marrow were obtained after informed consent from 20 patients with multiple myeloma, at diagnosis, during intermittent chemotherapy and after treatment. Samples are numbered sequentially, e.g. JOD-1, JOD-6, etc. Peripheral blood was drawn into heparinized tubes and purified over Ficoll Paque (Pharmacia, Dorval QB) as previously described (Bergsagel et al., 1995) to give peripheral blood mononuclear cells (PBMC). Bone marrow cells (BMC) were also purified using Ficoll Paque. All samples were purified immediately after being drawn, and were stained for cell sorting (as outlined below) and fixed within 4 hours after collection, to preserve mRNA. Samples for in situ RT-PCR were stored for up to 24 hours in fixative prior to sorting. For single cell PCR and RT-PCR, all samples remained unfixed, were stained, sorted and processed within 4 hours post-collection of the sample.

Antibodies and reagents: FMC 63 (CD19; a diagnostic marker for B cells; Pietersz et al, 1995; Zola et al., 1991) was conjugated to FITC. Leu-4PE (CD3; a diagnostic marker for T cells) and Leu17-FITC (CD38; a diagnostic marker for plasma cells) were from Becton Dickinson (San Jose, Calif.). Ig2a-PE, IgG1 and goat anti-mouse Ig-PE were from Southern Biotech (Birmingham, Ala.). Anti-human Ig F(ab)2 fragments coupled to PE and F(ab)2 fragments of goat-anti-mouse PE were from Southern Biotech.

Immunoflourescence (IF) and cell sorting: Staining for surface phenotype utilized 1 or 2 color IF with CD19-FITC and CD3-PE, as described in Pilarski and Belch, 1994 and Bergsagel et al., 1995. All experiments included controls with isotype matched monoclonal antibodies. CD19+ and CD3+ subsets of PBMC were sorted using the ELITE (Coulter, Hialieh, Fla.). BMC were stained with CD38-FITC and anti-human Ig-PE followed by sorting of the cells with high forward and side scatter that were stained by both CD38 and Ig reagents. Sort gates were set to include only those cells with staining brighter than the relevant isotype controls, as previously described (Bergsagel et al., 1995). For single cell experiments, individual CD19+ PBMC or CD38$^{hi}$ large BMC were sorted into individual wells of a microtitre plate, or directly into 0.2 ml thin walled PCR tubes. On reanalysis, sorted CD19+ populations had a purity of 95% or greater for the defining phenotype. PBMC had no detectable contamination with any peripheral plasma cells as defined by their relatively low cytoplasmic Ig content (Bergsagel et al., 1995), and the absence of morphologically identifiable plasma cells in cytospins of sorted subsets, in cytospins of PBMC or in smears of patient blood. To avoid any contamination between samples, and in particular to avoid contamination of blood cells with BM cells, blood samples were always sorted prior to bone marrow samples, and tubing in the flow cytometer was always washed with bleach between sorts.

After Ficoll partial purification of BMC, the BMC can be further separated into B or T cells or plasma cells using antibody coated columns and these cells. Any of these populations of cells could be diluted using limiting dilutions to yield one cell per well and this procedure could be used in place of flow cytometry.

Morphology of sorted CD19+ MM PBMC: Sorted CD19+ PBMC were place on slides, and were stained with Wright's stain. Slides were examined microscopically for morphological characteristics.

Patient-specific amplification (PSA): For amplification of patient-specific sequences, primers to CDR2 and CDR3 regions of the rearranged IgH VDJ from individual BM plasma cells were designed and used for in situ RT-PCR. This was found to be more specific than was the use of a CDR3 primer paired with a consensus FR2 primer. PSA utilized a primer from the 5' terminus of the CDR2 region paired with a primer to the entire CDR3 region. The sequences for patients JOD and LAR PSA primers are given in Table 1 (SEQ ID NOS.8–11). Primer sequences were designed based on the IgH VDJ sequence present in the majority of individual BM plasma cells. For all patients, the CDR2/CDR3 amplification was done using autologous T cells as a negative control, and the specificity of the amplification was confirmed by testing the primers on B cells from an unrelated patient. For JOD, the sequences used in PSA were detected in DNA from 10/11 single BM plasma cells. For LAR, the presence of the clonotypic sequence was confirmed in the mRNA from 42/48 individual sorted LAR BM plasma cells using single cell RT-PCR with patient-specific CDR2/CDR3 PSA giving a product of the expected size, 162 base pairs.

Single cell PCR: Single cells were sorted into 0.2 ml PCR tubes assembled on a Micro Amp base (Perkin Elmer, Mississauga, ON). Each of the tubes contained 5 ml of lysis solution (200 mM KOH, 50 mM DTT). After sorting, tubes were incubated in a thermal cycler (Perkin Elmer) for 10 minutes at 65° C. followed by addition of 5 ml of neutralizing solution (900 mM Tris-HCl pH 9.0, 300 mM KCl, 200 mM HCl). Next, 40 ml of a PCR mix (0.1 mM dNTPs [Boehringer Mannheim, Laval QB], 10 mM Tris-HCl pH9.0, 0.1% Triton-X-100, 2 mM MgCl2, and 5 units of TAQ polymerase [Gibco/BRL, Burlington ON] containing 0.01 mM of both FR2 and JH1 primers [see Table 1], was added to each sample. Samples were cycled as follows: 180 seconds at 95° C. (initial denaturation step), followed by 40 cycles of 30 seconds at 94° C., 30 seconds at 52° C., and 60 seconds at 72° C., followed by a 10 minute terminal incubation at 72° C. For consensus amplification, two ml of each sample was then transferred into a second PCR tube containing 48 ml of a PCR mix as above containing 0.01 mM of both FR2 and JH2 primers, and cycled as above. For patient-specific amplification (PSA) with single cells, the second round of amplification was performed as above, except with PCR mix containing 0.01 mM of both CDR2 and CDR3 primers instead of the consensus FR2 and JH2 primers, and a higher stringency annealing temperature of 60° C., instead of 52° C. The final products were analyzed by electrophoresis through 6% polyacrylamide gels or on 2% agarose gels in 0.5×Tris/Boric Acid/EDTA (TBE) buffer (Sambrook et al., 1989), followed by ethidium bromide staining of the gels, and visualization of bands under UV light.

Single cell RT-PCR: Single cells were sorted into 0.2 ml PCR tubes as for single cell PCR, above. Each tube contained 4 ml of RT-Lysis solution (SuperScript first strand buffer from Gibco/BRL [0.25 M Tris-HCl (pH 8.3), 0.37 M KCl and 15 mM $MgCl_2$], 0.5% NP-40, 0.01 M DTT, 0.25 mM dNTPs, 200 units of RNAse inhibitor, and 0.006 mMdT16 (a universal poly dT primer). After sorting, the samples were heated to 70° C. for 10 minutes, placed on ice, and 1 ml (10 units) of reverse transcriptase (SuperScript, Gibco/BRL) was added to each tube. The tubes were incubated at 42° C. for 30 minutes, and the reactions were stopped by heating at 99¼C for 3 minutes. Two ml of synthesized cDNA were transferred into fresh PCR tubes containing 48 ml of PCR mix (0.1 mM dNTPs, 10 mM Tris-HCl pH 8.3, 2 mM MgCl2, 2 units of TAQ polymerase) containing 0.01 mM each of FR2 and JH1 primers. Samples were heated for 3 minutes at 95° C., followed by 25 cycles of 30 seconds at 94° C., 30 seconds at 52° C. and 1 minute at 72° C. For consensus PCR, 2 ml of this PCR-amplified mixture were transferred into a third tube containing 48 ml of the PCR mix containing 0.01 mM of both FR2 and JH2 primers, and cycled as above for 25 cycles. For PSA, this final amplification was performed as above, except with patient-specific CDR2 and CDR3 primers and an annealing temperature of 60° C. The final products were analyzed by electrophoresis through 2% agarose gels in 0.5×TBE buffer, followed by ethidium bromide staining of the gels, and visualization of bands under UV light.

In situ RT-PCR: In situ reverse transcriptase polymerase chain reaction (RT-PCR) (Nuovo, 1994) was used to quantitate the proportion of sorted PBMC expressing IgH mRNA, CD19 mRNA and clonotypic VDJ rearrangements. PBMC from MM patients were stained in double direct immunofluorescence with monoclonal antibody to CD19 (CD19-FITC) and to T cells (CD3-PE), and fixed in 10% formalin/PBS overnight. Using the ELITE Autoclone (Coulter), each PBMC sample was sorted at 10,000 cells per well of a flat bottom 96 well microtitre tray into T (CD3+ 19−) and B (CD3−19+) fractions. For some samples the whole blood lysis method (Becton Dickinson) was used to prepare cells for the in situ RT-PCR, as well as unfractionated PBMC. Rapid processing prior to the fixation step was essential to preserve mRNA. Samples were placed in 3 spots, at 10,000 cells per spot, on In situ PCR glass slides (Perkin Elmer) and air dried. Cells were permeabilized using 2 mg pepsin (Boehringer Mannheim) per ml of 0.01N HCl. The time of pepsin digestion was carefully optimized. Pepsin was inactivated to a 1 minute wash in DEPC (diethylpyrocarbonate)-treated water, followed by a 1 minute wash in 100% ethanol. Digestion with 1000 U/ml of DNAseI (RNAse-free, Boehringer Mannheim) removed genomic DNA prior to reverse transcription. Incubation of the sample with DNAseI was performed in the In situ PCR System (Perkin Elmer) thermal cycler at 37° C. overnight. DNAseI was removed by a 1 minute wash in DEPC-treated water followed by a 1 minute wash in 100% ethanol. In situ reverse transcription was performed to 60 minutes at 37° C. only for the test samples under standard conditions recommended by the manufacturer using SuperScript (Gibco/BRL) and the universal primer, dT16. After washing with water and ethanol, an In situ Core Kit (Perkin Elmer) was used to amplify a target sequence during 25–30 cycles (94° C. for 1', 56° C. for 1' and 72° C. for 1.5') with a direct incorporation of DIG-11-dUTP (Boehringer Mannheim) during PCR to label the product. Amplified DNA was detected using anti-DIG Fab conjugated with alkaline phosphatase (Boehringer Mannheim), followed by incubation with NBT/BCIP substrate solution vitro blue tetrazolium chloride/5-Bromo4-chloro-3indolyl-phosphate, 4-toluidine salt, Boehringer Mannheim). Color development was monitored under the microscope. Negative controls for every sample included omitting the RT step to confirm digestion of genomic DNA which would otherwise lead to amplification of non-specific PCR products. As a positive control, mRNA for a housekeeping gene, histone, was amplified to quantitate the number of cells on the slide with intact mRNA. As a control for the specificity of the primers used to amplify IgH mRNA and CD19, autologous T cells were tested and were negative for both IgH and CD19 mRNA, as expected. Primer pairs are given in Table 1. IgH mRNA was detected using consensus primers to FR2 (SEQ ID NO.5) and JH (SEQ ID NOS.6 and 7).

RT-PCR using bulk RNA: RNA was prepared from $0.1–10×10^6$ unfractionated BMC, PBMC or sorted populations of B and T cells of the same patient using Trizol (Gibco/BRL) according to manufacturer's directions. (The T cells, collected at the same time as B cells in a double immunofluorescence sort, serve as a negative control.) After purification, 1 microgram of RNA was reverse transcribed using SuperScript reverse transcriptase (Gibco/BRL) and the universal primer oligo $dT_{15}$ using manufacturers instructions. Briefly, RNA was incubated with the primer for 10' at 70° C., chilled on ice and 5×First Strand Buffer (Gibco/BRL), 0.1M DTT, 0.25 mM dNTPs and 200U SuperScript reverse transcriptase were added. The reaction tube was placed at 42° C. for 30', followed by heating for 3' at 100° C. PCR was performed under standard conditions. Briefly, 2 ml cDNA from the reverse transcriptase reaction was added to 48 ml of PCR Buffer (Gibco/BRL), containing 2 mM $MgCl_2$, FR2 and JH1 primers as described above for single cell RT-PCR, and 1U TAQ polymerase. Samples were cycled on the Perkin Elmer Thermal Cycler 9600 for 25 cycles of 30 seconds at 94° C., 30 seconds at 50° C. and 45 seconds at 72° C. For consensus RT-PCR, a second round of amplification was carried out using FR2 and JH2 primers, and cycling as above. For PSA, the second round of amplification utilized patient specific primers CDR2 and CDR3 for 25 cycles at an annealing temperature of 60° C. The PCR products were analyzed by electrophoresis on 2% agarose gels in TBE buffer. The gels were stained with ethidium bromide, and bands were visualized with UV light.

DNA Sequencing: Sequencing was performed using techniques well known in the art, with $a^{32}P$-dCTP (Amersham, Oakville ON) using either the Sequenase 2.0 system (Amersham) or the cycle sequencing kit (Perkin Elmer) following the manufacturer's instructions. For patient JOD, the FR2/JH2 PCR product was subcloned into a Bluescript vector expressed in the DH5 strain of *Escherichia coli*, purified, and sequenced using universal sequencing primers. For LAR, the FR2/JH2 product was digested from the low melting point gel using b-Agarase (New England Biolabs, Mississauga ON) according to the manufacturers directions, and sequenced directly using the FR2 and JH2 primers. The products of sequencing were analyzed and aligned using GCG and NCBI BLAST programs.

EXAMPLE 1

PATIENT JOD

Amplification of Rearranged IgH Sequences in MM PBMC CD19+ Cells and Bone Marrow Plasma Cells Using IgH Consensus Primers.

Figure 2:
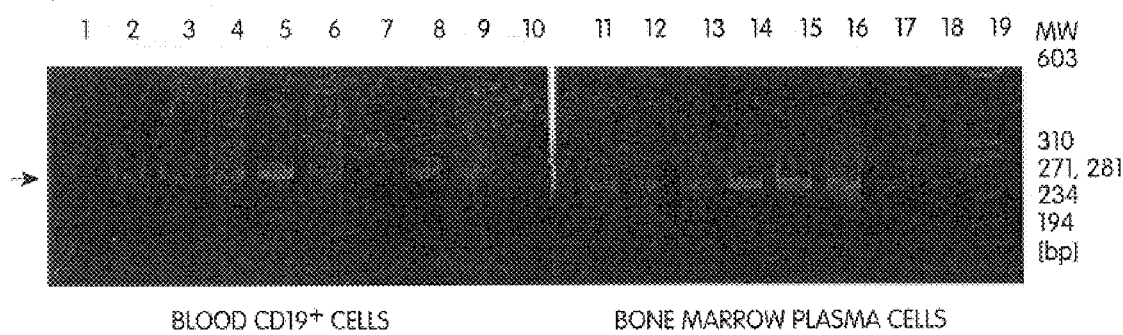
FIG. 2 is a photograph illustrating the detection of amplified IgH rearrangements using consensus primers in single plasma cells and single B cells from a multiple myeloma patient 6 months after chemotherapy. PBMC from patient JOD-5 were taken one month after completing 6 cycles of chemotherapy. PBMC were stained with CD19-FITC and individual CD19+ cells were deposited into lysis buffer in PCR tubes using the ELITE Autoclone cell deposition unit. DNA was amplified using hemi-nested consensus primers designed to detect IgH rearrangements. BMC were stained with CD38-PE and anti-human Ig-FITC and CD38+ cells with high forward and side scatter were sorted into PCR tubes. Lane 19 contained molecular weight standards. Lane 1 contained a "water control" for the first step of the consensus PCR. Lanes 2–9: bands amplified from single CD19+ PBMC. Lanes 11–18: bands amplified from single BM plasma cells.

Substantial numbers (mean=28–33% (Bergsagel et al, 1995)) of CD19+ PBMC are detectable in PBMC of multiple myeloma patients (Pilarski and Jensen, 1992; Bersagel et al., 1995; Pilarski et al., 1996). A B cell is definitively identified by its rearranged immunoglobulin genes and usually by the expression of Ig mRNA. To confirm that the CD19+ PBMC obtained by cell sorting are in fact B cells, single CD19+ PBMC from MM patient JOD were examined for rearranged Ig genes. Single CD19+ cells were sorted into PCR tubes and the DNA encoding the Ig heavy chain was amplified using PCR with hemi-nested consensus framework primers to FR2, JH1 and JH2 (Table 1, SEQ ID NOS.5–7). A product of the expected size, about 160 base pairs, was amplified from patient JOD (FIG. 2), whose PBMC comprised 30% CD19+ cells. Sequencing followed by BLAST search indicated that all bands had an IgH V region sequence. Single bone marrow plasma cells from the same patient were also amplified using the same consensus primers. All plasma cells examined, 11/11, gave bands that comigrated with those produced upon amplification of the CD19+ cells (FIG. 2). Thus, all CD19+ PBMC and all BM plasma cells analyzed had a rearranged IgH CDR3.

Identification of the Clonotypic Rearrangement.

To confirm that the product amplified in single cell PCR was in fact IgH, and to determine whether or not the rearranged IgH CDR3 sequence of BM plasma cells was shared by CD19+ PBMC, the bands shown in FIG. 2 as well as additional bands from another gel, were excised and sequenced from both the FR2 and JH directions. The BM plasma cell clonotypic rearrangement for patient JOD was identified as that sequence shared by the majority of plasma cells examined. Ten out of eleven of the individual BM plasma cells had an identical IgH rearrangement, providing proof that this was the monoclonal JOD myeloma rearrangement (FIG. 3A). This rearrangement aligned with the DP31 VH3 gene family (FIG. 3A). Of the CD19+ PBMC B cells from JOD-5 (taken at month 7 after diagnosis), 9/10 had an IgH CDR3 sequence identical to that of the autologous BM plasma cells with little or no intraclonal variation. Representative PBMC B and BM plasma cell sequences are presented in FIG. 3A (SEQ ID NO.67–70) aligned with the DP-31 sequence (SEQ ID NO.66). One B cell had an unrelated sequence that was of a different V gene family (VH4a) (FIG. 3B). The unrelated BM plasma cell aligned with the DP-31 VH3 sequence, but had low homology to the JOD consensus sequence (FIG. 3B). Thus, for patient JOD, who had just completed 6 cycles of VAD chemotherapy, 9/10, or 90%, of blood B cells were clonotypic. The absolute number of B cells in blood for sample JOD-5 was 0.58× $10^9$/L of blood, and of these 0.52×$10^9$/L were clonotypic. Thus clonotypic cells in blood represented 8.6% of total white blood cells.

The clonotypic PCR primers for JOD were prepared based upon the sequence information obtained from the single R,and are shown in Table 1 (SEQ ID NOS.8–11).

To confirm that the sequences identified as clonotypic for JOD were actually expressed as mRNA, sorted B cells (CD19+) were analyzed using in situ RT-PCR to amplify the clonotypic sequence using patient specific primers (hereinafter referred to as patient-specific amplification, PSA). Sorted B and T cells were analyzed from patient JOD-6, at 11 months post diagnosis (5 months after cessation of chemotherapy). To confirm specificity of the JOD PSA, B and T cells from an unrelated MM patient were also tested. All circulating B cells expressed CD19 mRNA. For two separate aliquots of JOD-6 B cells, a mean of 71% expressed clonotypic mRNA (Table 2). T cells from JOD-6 had 1% of clonotypic cells, indicating a low level of contamination by B cells. However, T cells from two different unrelated patients had less than 0.1% clonotypic cells, and B cells from unrelated patients had 4% or less positive cells, perhaps reflecting limited diversity in the few normal B cells circulating in MM (Pilarski et al., 1984; Pilarski et al., 1985), and confirming the specificity of the patient-specific primers for JOD. Thus, clonotypic B cells, as defined by patient-specific IgH rearrangement and mRNA synthesis, are not eradicated by chemotherapy, and persist for prolonged periods after cessation of therapy. For JOD-6, B cells numbered 0.22×$10^9$/L of blood , and 0.15×$10^9$/L were clonotypic (3.3% of total WBC). As further confirmation that patient sample JOD-6 had circulating clonotypic B cells at 5 months post-chemotherapy, DNA from single sorted B cells was amplified by PSA using CDR2/CDR3 primers. Nine out of 27 individual B cells bad a DNA rearrangement that was amplified by the JOD PSA to give products of the expected size, 160 base pairs, as shown in FIG. 4A.

Figure 4A:
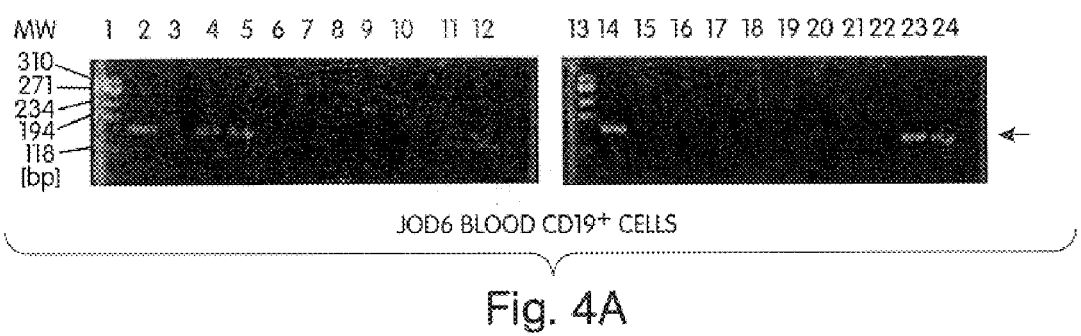
FIG. 4 depicts patient-specific amplification (PSA) using CDR2 and CDR3 primers specific for the JOD clonotypic VDJ rearrangement. Blood was taken at 12 months post-diagnosis from patient JOD (JOD-6). DNA from 27 single sorted B cells were amplified in a two step PCR. The initial amplification was carried out with consensus primers, followed by 40 cycles of PSA PCR using primers homologous to the CDR2 and CDR3 sequences (Table 1, SEQ ID NOS.8 and 9, respectively) of the JOD clonotypic sequence identified in FIG. 3 (SEQ ID NO.72). The PSA step of PCR was at high stringency (60¼C). (A) shows that a product of the expected size was amplified from 9/27 individual B cells. (B) gives the sequence (SEQ ID NO.75) of the product amplified by the CDR2 and CDR3 primers from 6 of the 9 B cells from which a patient-specific band was amplified.

The bands amplified in FIG. 4A were sequenced to confirm that they indeed represented the JOD clonotypic sequence, thus validating the use of PSA in quantitating clonotypic cells in blood After amplification with primers to CDR3 and the 5' terminus of CDR2 from JOD, the amplified products from 5/5 individual JOD-6 B cells had nearly identical sequences in the intervening FR2 region, and identical sequences from the 25 base pairs of CDR2 not part of the primer sequence (FIG. 4B (SEQ ID NO.75)). Thus PSA is specific. Using PSA, a product of the expected size was amplified from bulk DNA isolated from BMC taken at diagnosis (JOD-4), from the staging BMC (JOD-5) and from a stable phase BMC (JOD-7), as well as from PBMC B cells but not from PBMC T cells from JOD-7, indicated persistence of the clonotypic sequence for over a year post-diagnosis (data not shown).

EXAMPLE 2

PATIENT LAR

Identification of the Clonotypic Sequence for LAR.

Figure 5A:
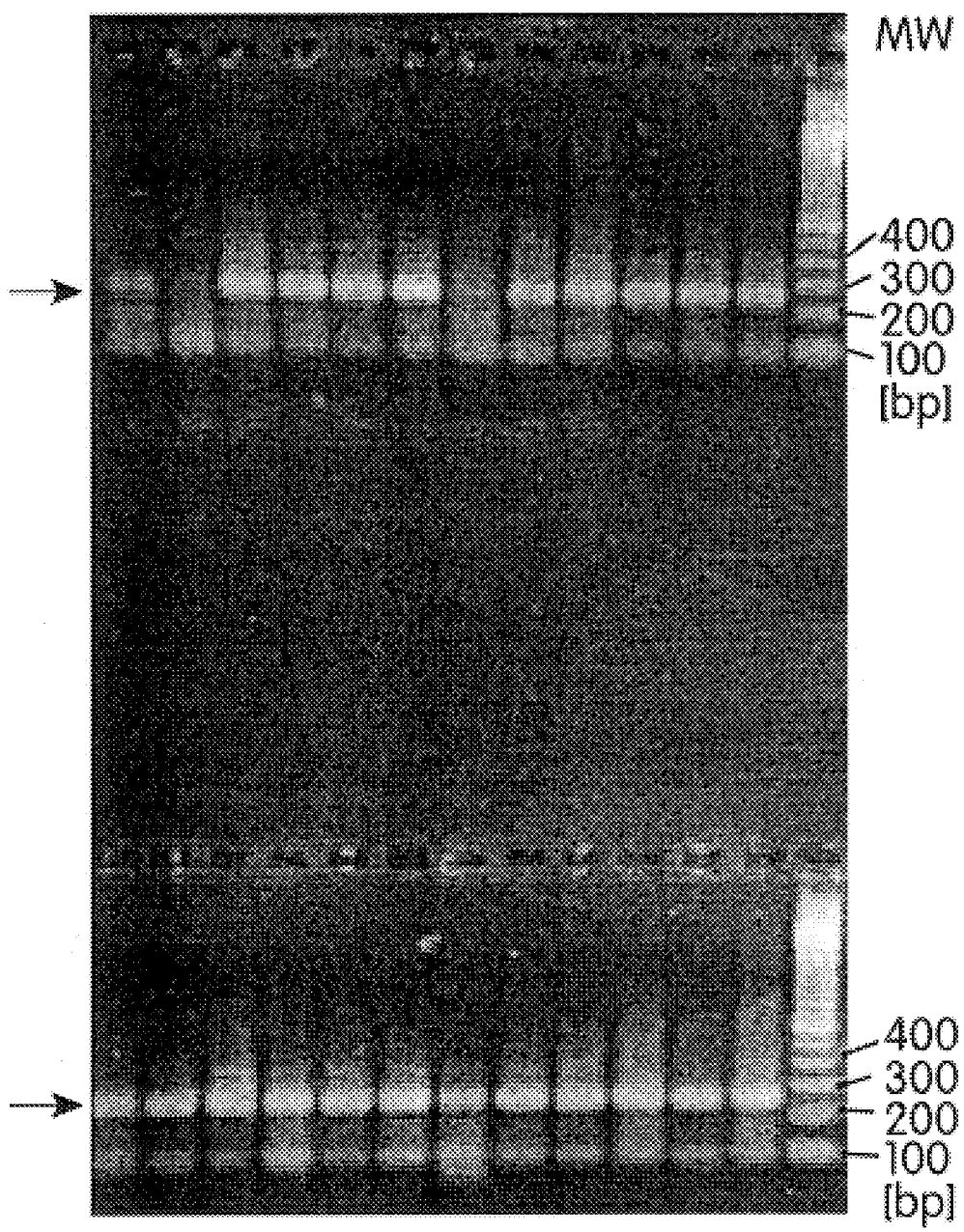
FIG. 5 shows the use of consensus primers in single cell RT-PCR to amplify IgH rearrangements from patient LAR BM plasma cells, the sequences obtained from the resulting PCR products, and the use of patient-specific primers derived from the sequence to amplify clonotypic sequences in single cells. (A) BMC from LAR, taken at diagnosis, were stained and individual plasma cells were sorted into PCR tubes. mRNA was amplified at relatively low stringency using hemi-nested consensus RT-PCR. (B) The CDR2 to CDR3 sequence of LAR (SEQ ID NO.76). Bands from (A) were cut out and sequenced. For 3/3 BM plasma cells the same VDJ sequence was obtained. (C) To confirm the number of single plasma cells expressing the sequence identified in (B) (SEQ ID NO.76), primers homologous to the patient-specific CDR2 and CDR3 regions were designed (Table 1) and used at high stringency to amplify mRNA from 48 individual BM plasma cells. 42/48 amplified a product of the expected size, confirming the sequence of (B) (SEQ ID NO.76) as clonotypic for LAR.
Figure 5C:
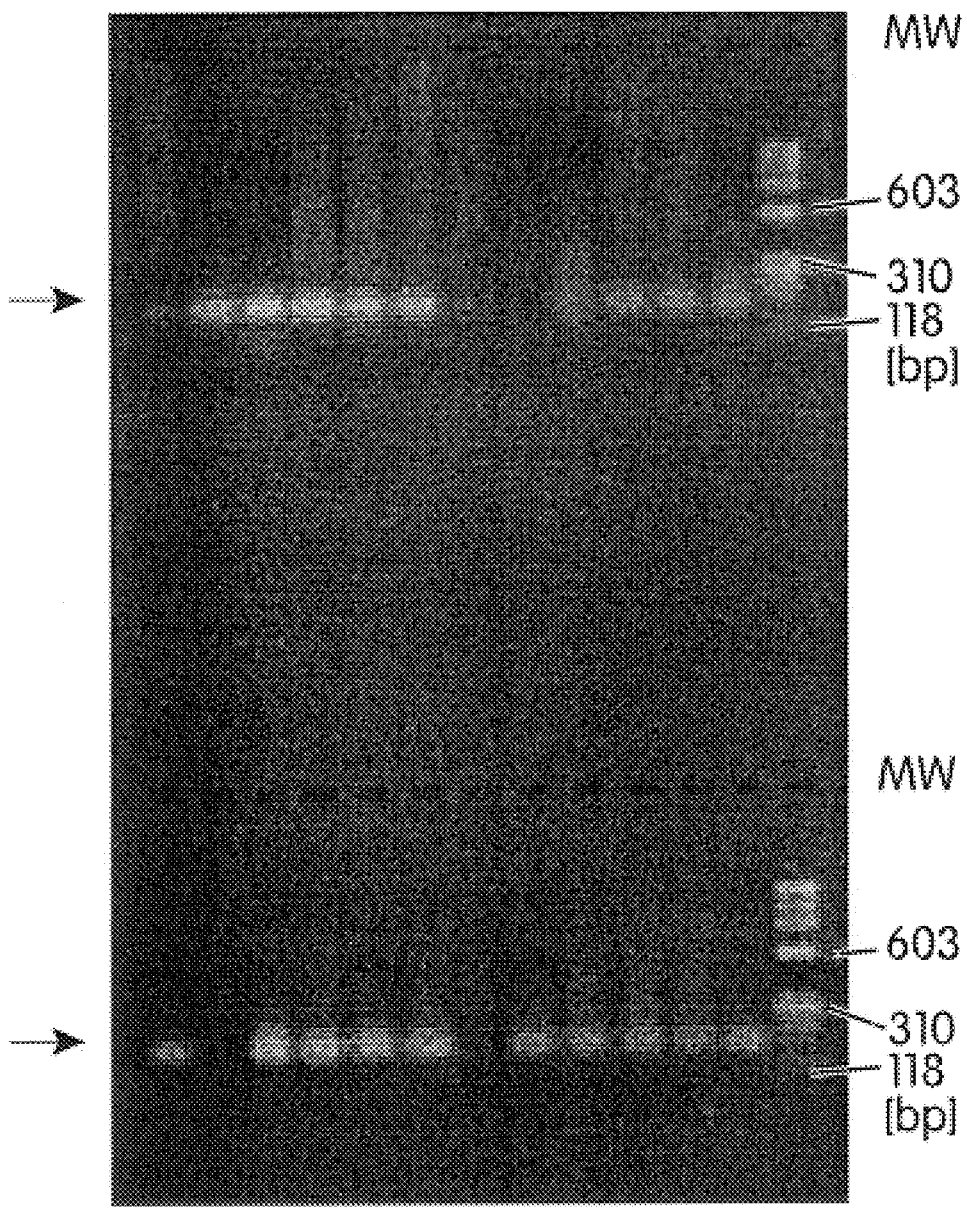

Individual BM plasma cells from newly diagnosed MM patient LAR were sorted into PCR tubes and the expressed IgH allele was amplified in RT-PCR using the consensus framework IgH primers shown in Table 1 (SEQ ID NOS.5–7). A product of the expected size was amplified in 36/36 individual BM plasma cells (FIG. 5A). Sequencing of the amplified bands from 3 of these plasma cells indicated that they had an identical VDJ sequence, shown in FIG. 5B (SEQ ID NO.76), that aligned with DP-79 of the VH4 family. CDR2/CDR3 LAR-specific primers, designed based on the plasma cell sequence, were used to amplify the mRNA from 48 additional BM plasma cells; 42/48 amplified a product of the expected size, shown in FIG. 5C, confirming the identity of the clonotypic sequence in the majority (48/51 or 88%) of individual plasma cells.

Quantitation of the Proportion of Clonotypic Cells Using PCR and in situ RT-PCR

To quantitate the proportion of blood B cells with clonotypic DNA rearrangements, single cell PSA PCR was used to amplify DNA from LAR-1 CD19+ B cells using LAR-specific primers. A clonotypic product was amplified from 4/12 (33%) individual LAR B cells. This sample was taken at diagnosis prior to initiation of treatment. To quantitate the number of LAR peripheral blood B cells expressing clonotypic mRNA sequences, in situ LAR PSA was used to amplify clonotypic mRNA from LAR B cells and, as a control, LAR T cells. The results are shown in Table 3. All aliquots of B and T cells expressed histone mRNA, a housekeeping gene product which was used to provide a measure of the number of cells which had intact and detectable mRNA. For the B cell aliquots, all B cells expressed CD19 mRNA, as well as IgH mRNA (detected by consensus primers). For LAR-1, in situ RT-PCR with LAR CDR2/CDR3 primers amplified a product in 522/1183 (44%) of sorted CD19+ blood B cells. This confirms at the mRNA level the finding that 4/12 LAR-1 B cells had clonotypic DNA rearrangements. T cells from LAR, not expected to express rearranged IgH, had less than 0.1% positive cells. For LAR-3, 46% of blood B cells were clonotypic (Table 3). LAR-1 was taken 2 months before initiation of therapy; LAR-3 was taken one month after initiation of therapy. Thus, for this patient, chemotherapy did not eradicate clonotypic blood B cells. Overall, the number of clonotypic B cells was reduced approximately 2 fold by one cycle of chemotherapy (from $0.12 \times 10^9$/L to $0.06 \times 10^9$/L).

Quantitation of Clonotypic Cells Using Unfractionated WBC.

In order to accurately determine the total number of circulating clonotypic B cells in MM, as well as to design a PSA assay which would be easily adaptable for clinical use, in situ RT-PCR using consensus IgH primers, as well as PSA with CDR2/CDR3 primers was performed on white blood cells prepared by the whole blood lysis method. The results are shown in Table 4. As predicted by previous work (Bersagel et al., 1995), approximately 3–10% of total WBC express CD19 and IgH mRNA. In situ RT-PCR amplification with IgH VDJ consensus primers of mRNA in WBC gave a mean of 5% for 5 different patients, with a range of 3.3% to 7.4%. Use of CD19 primers to amplify mRNA from WBC gave a mean value of 6.8% for 5 different patients, with a range of 2.5% to 10.4% of WBC. To determine the frequency of clonotypic cells among unfractionated WBC, PSA in situ RT-PCR with LAR primers was used. For LAR-3, in situ RT-PCR using unfractionated WBC prepared by the red cell lysis method for WBC demonstrated that 145/2116 WBC, or 6.8% of total WBC were CD19+. To determine the number of circulating clonotypic cells, LAR WBC were amplified using PSA with CDR2 and CDR3 primers. By this measure, 24/1987 WBC, or 1.2% of LAR-3 WBC were clonotypic, confirming calculations from Table 3. The infrequent presence of either LAR or JOD sequences among WBC from unrelated MM patients confirms the specificity of the assay. The simplicity and quantitative nature of PSA using in situ RT-PCR on total WBC makes this approach feasible in a clinical laboratory, for monitoring circulating relatives of the malignant myeloma clone during treatment. It is also a validation of more complex methods for determining the frequency of clonotypic B cells that rely on purified B cell populations. Calculated values from purified populations appear to reasonably estimate the absolute numbers obtained by analysis of unmanipulated WBC.

Specificity of JOD and LAR PSA.

Figure 6:
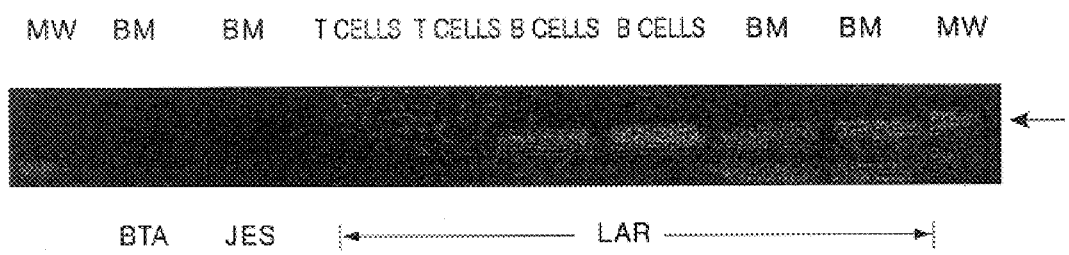
FIG. 6 demonstrates the specificity of LAR patient-specific primers. Clonotypic LAR sequences are amplified in bulk RT-PCR from unsorted LAR BMC and from sorted LAR blood B cells but not from LAR blood T cells, or from BMC of unrelated patients. RNA was amplified from unsorted BMC, from sorted PBMC B cells and from sorted PBMC T cells using patient-specific CDR2/CDR3 primers (Table 1, (SEQ ID NO.8–11) at high stringency.

Total RNA from sorted LAR B cells, T cells and BM plasma cells, as well as BM plasma cells from 2 unrelated MM patients, was amplified in conventional bulk RT-PCR. An amplified product of the expected size was detected in B and plasma cells from LAR, but was absent from LAR T cells and from BM plasma cells of two unrelated MM patients (FIG. 6), confirming the specificity of the LAR primers, and the presence of clonotypic mRNA within the B cell population. The identity of the PSA RT-PCR product for LAR B and plasma cells was confirmed by analysis of the products using restriction fragment length polymorphism (not shown). Control experiments also demonstrated that JOD primers did not amplify a product from LAR blood subsets of BMC in bulk RT-PCR, and LAR primers did not amplify a band from JOD-5, JOD-6 or JOD-7 PBMC, PBMC subsets or BMC (not shown). Results identical to those for LAR-1 showing the presence of clonotypic sequences in BMC and PBMC B cells, but not PBMC T cells, were obtained for LAR-3 using bulk PSA of mRNA (not shown).

Discussion of Results.

The above examples demonstrate that in MM patients, 44–90% of total circulating blood B cells, or 1–9% of total WBC have an IgH rearrangement identical to that of autologous BM plasma cells, the tumor cells. The absolute number ranges from $0.06–0.5 \times 10^9$ clonotypic cells/L of blood. An important aspect of this work is the identification of the clonotypic IgH sequence as that expressed by the majority of individual BM plasma cells in a patient. This type of quantitation is possible only at the single cell level, either by single cell PCR or RT-PCR, or by in situ RT-PCR. Although previous studies analyzed homogenized preparations of nucleic acid derived from unfractionated bone marrow, the assumption was made that most plasma cells express the IgH sequence identified as predominant in bulk PCR or RT-PCR. Confirmation of this was essential, since only an IgH CDR3 sequence that identifies most BM plasma cells would be expected in the blood. Using single cell PCR or RT-PCR, for patient JOD and LAR, 10/11 and 45/51 respectively of BM plasma cells expressed the sequence identified as clonotypic. A second refinement in this work was the use of two patient specific primers, CDR2 and CDR3, for amplification of clonotypic sequences. The inventors found that use of a primer specific for patient-specific CDR3 together with a consensus FR2 primer, as commonly used in other studies (allele-specific oligomer (ASO)-PCR), was less specific than was the use of PSA with CDR2/CDR3 primers to drive high stringency amplification of IgH variable regions. The patient-specific amplification (PSA) methods were validated by the inventors demonstration that the sequences of CDR2/CDR3 amplified products from 6 individual B cells were clonotypic. For patient JOD, the presence of the clonotypic sequence was confirmed in 3 different samples of BM plasma cells taken over a 1.3 year period including at diagnosis (JOD-4), for staging after chemotherapy (JOD-5), and during the stable phase of disease (JOD-7). The clonotypic JOD sequence was detectable in PBMC or in purified B cells from 4 sequential JOD samples.

For all patients tested, all CD19+ (by cell sorting) blood B cells expressed both CD19 mRNA and IgH mRNA. Based on mean values from phenotypic analysis of nearly 500 patients done previously, the absolute numbers of circulating blood B cells represent about 3–10% of total WBC, or about 0.4×10⁹ B cells/L of blood (unpublished results and Bergsagel et al., 1995). For patient JOD at 1 month post-chemotherapy (JOD-5), 90% of individual circulating B cells hare an IgH VDJ rearrangement identical to that of autologous BM plasma cells. However, for JOD-6, taken 5 months after cessation of therapy, the absolute number and proportion of clonotypic B cells decreased, suggesting recovery of polyclonal B cells post-chemotherapy, and by extrapolation that chemotherapy may actually enrich for clonotypic B cells, although absolute numbers may decrease. This may reflect a greater chemosensitivity for normal B cells as compared to the clonotypic set. For patient LAR-1, at diagnosis, 44% of circulating B cells were clonotypic. After one cycle of chemotherapy, the proportion of clonotypic B cells remained constant, although absolute numbers decreased suggesting depletion after the initial exposure to chemotherapy.

For patient LAR, newly diagnosed, about 44% of total CD19+ B cells are clonotypic. For JOD, after 6 cycles of chemotherapy, nearly all B cells (90%) were clonotypic. At 5 months (JOD-6) post-chemotherapy, 71% of blood B cells were clonotypic, indicating their persistence after chemotherapy. Calculations of the absolute number of clonotypic B cells circulating the blood of these two patients give values of 1–9% of white blood cells or $0.06-0.52 \times 10^9$ clonotypic B cells/L of blood comparison with normal values indicates expanded numbers of overall B cells, and enriched proportions of monotypic B cells. Sequential samples for both JOD and LAR indicate that chemotherapy does not effectively target circulating clonotypic B cells.

The long term goal of this work is to evaluate the link between clonotypic B cells, disease progression and spread, and clinical outcome. The frequent relapse rate for myeloma indicates that current modes of treatment are not accompanied by elimination of the generative compartment of MM. PSA for monitoring clonotypic cells in whole blood using in situ RT-PCR or limiting dilution PCR with patient-specific primers proves a clinically feasible monitoring strategy for determining the extent to which clonal cells infiltrate the blood of MM patients before, during and after therapy, as well as their persistence after cytoreduction and transplantation. Measurement of circulating clonotypic B cell numbers using in situ PSA provides a marker of blood involvement that complements measure of plasma cell kill, to evaluate the efficacy of present and future therapies which target the malignant clone in MM. This assay allows the use of blood tests rather than the more invasive and expensive bone marrow tests for routine clinical monitoring. When bone marrow or tissue samples are necessary, this assay is quantitative, more specific and more sensitive than any currently available test.

EXAMPLE 3

ANALYSIS OF ADDITIONAL MYELOMA PATIENTS

The aforementioned methods for determining the frequency of clonotypic B cells in blood was applied to a group of 18 multiple myeloma patients. This example clearly demonstrates how the methods of the invention are used to monitor the number of clonotypic B cells before, during and after treatment by chemotherapy or hematopoietic transplantation.

The characteristics of the clonotypic sequences derived from BM plasma cells of the patients are presented in Tables 4 and 5. The patients have the Ig isotype distribution characteristic of myeloma. The pattern of Vh family usage included frequent use of the Vh3 gene family and infrequent use of the Vh1 family (Table 4). The most frequent J segment was Jh4 (65% of the patients). Overall, the CDR3 length was 12–54 nucleotides (NT) (mean +/–SE=28+/–2 NT). The sequences of the CDR3 portion of IgH are presented in Table 5 (SEQ ID NOS.30–47).

9–90% of Myeloma PBMC B Cells are Clonotypic as Detected by in situ RT-PCR

For 17 myeloma patients (one patient from Table 4 died prior to this analysis) and 35 blood samples analyzed in this study, the percentage of circulating B cells expressing clonotypic mRNA was on average 66%. Table 6 records the frequency of clonotypic B cells for each myeloma patient for one or more blood samples taken at regular clinical visits. In all cases the sequences identified as clonotypic were confirmed to be expressed by >80% of autologous BM plasma cells. In blood, the proportion of B cells expressing clonotypic IgH mRNA ranged from 9–90% with a mean of 66%+/–4% (SE). These values were used to calculate that 14+/–2% of PBMC were clonotypic cells (range=0.9–50% of PBMC)

The proportion of clonotypic cells among total white blood cells was calculated as 3.5+/–1% (range=1–9%) (data not shown). The absolute number of circulating clonotypic B cells was $0.15+/-0.02 \times 10^9$/L of blood (range=0.01–0.61× $10^9$/L).

| Abbreviations | |
|---|---|
| BMC | bone marrow cells |
| dNTP | deoxynucleotide triphosphates |
| PBMC | peripheral blood mononuclear cells |
| MGUS | monoclonal gammopathy of undetermined significance |
| MM | multiple myeloma |
| IgH | immunoglobulin heavy chain |
| VDJ | variable, diversity, joining |
| WBC | white blood cells |
| PSA | patient-specific amplification |
| TCR | T cell receptor |
| FITC | Fluorescene isothiocyanate |
| PE | phycoerytherin |
| MW | molecular weight |
| BM | bone marrow |
| ALL | Acute Lymphocytic Leukemia |
| JOD, LAR, JES, BTA | Nomenclature for individual patients |
| CLL | Chronic Lymphocytic Leukemia |
| VAD | Vincristine, Adriamycin, Dexamethasone |
| M | Melphalan |
| Dex | Dexamethasone |
| UV | Ultraviolet |

TABLE 1

Primers used for in situ RT-PCR, for PCR and for RT-PCR

| | |
|---|---|
| Histone 5' | CCACTGAACTTCTGATTCGC |
| Histone 3' | GCGTGCTAGCTGGATGTCTT |
| CD19 5' | GACCTCACCATGGCCCCTGG |
| CD19 3' | CAGCCAGTGCCATAGTAC |
| Consensus IgH primers | |
| IgH FR2 5' | TATGAATTCGGAAAGGGCCTGGAGTGG |
| IgH JHI 3' | ACGGGATCCACCTGAGGAGACGGTGACC |
| IgH JH2 3' | ACGGATCCGTGACCAGGGTNCCTTGGCCCCAG |
| Patient-specific CDR2/CDR3 primers for PSA: | |
| JOD5 CDR2 5' | CGTGGAATAGGGGCAGTC |
| JOD5 CDR3 3' | AAGTTGTAGCCATCTCGG |
| LAR1 CDR2 5' | ACTTCTACGACAATGGCGAAAC |
| LAR1 CDR3 3' | CCCTCCGAGGACGTGGTG |

Note: the above sequences represent SEQ ID NOS: 1–11, respectively.

TABLE 2

PBMC B cells, but not T cells, express clonotypic sequences for patient JOD, after chemotherapy

| Patient | Tissue | Subset | % Clonotypic (# counted) | # × 10⁹/L of Blood | % of WBC Calculated |
|---|---|---|---|---|---|
| JOD-5 | BMC | CD38⁺Ig⁺ | 91 (10/11) | | |
| JOD-5 | PBMC | CD19⁺ | 90 (9/10) | 0.52 | 9 |
| JOD-6 | PBMC | CD19⁺ | 71 (1111/1555) | 0.15 | 3 |
| | | | 1.3 (6/463) | | |
| NKI-7 | PBMC | CD19⁺ | 3.7 (12/305) | 0.007 | 0.06 |
| | | CD3⁺ | <0.1 (0/1000) | | |
| RAM-9 | PBMC | CD19⁺ | <0.1 (0/1000) | <0.0006 | <0.01 |
| | | CD3⁺ | <0.1 (0/1000) | | |

PBMC or BMC were sorted as indicated and analyzed using PSA with in situ RT-PCR with primers specific for CDR2 and CDR3 of JOD (lines 3–11), or sequencing (lines 1 and 2). For sorted CD19+ PBMC from unrelated patients, the presence of B cells was confirmed using in situ RT-PCR for CD 19, and viability of mRNA was established using histone primers.

TABLE 3

PBMC B cells, but not T cells, have clonotypic IgH VDJ sequences for patient LAR, at diagnosis and after initiation of treatment

| Patient | Tissue | Subset (Sorted) | % Clonotypic | # × 10⁹/L of Blood | % of WBC (Calculated) |
|---|---|---|---|---|---|
| LAR-1 | BMC | CD38⁺Ig⁺ | 88 (45/51) | | |
| LAR-1 | PBMC | CD19⁺ | 44 (522/1183) | 0.12 × 10⁹ | 2.2 |
| | | CD3⁺ | 1 (5/452) | | |
| LAR-3 | PBMC | CD19⁺ | 46 (190/409) | 0.06 × 10⁹ | 1.1 |
| | | CD3⁺ | <0.1 (0/1000) | | |

PBMC and BMC were analyzed using PSA with CDR2 and CDR3 primers from patient LAR in in situ RT-PCR. In all cases, viability of mRNA was confirmed by amplification with primers to histone.

TABLE 4

Characteristics of Clonotypic IgH VDJ sequences

| Patient (status*) | IgH | Lt | % PCᵃ | Vh Family | Jh Family | CDR3 Length (NT) |
|---|---|---|---|---|---|---|
| 1. (Unt) | IgG | K | 23 | Vh2(S12-12) | Jh4(b) | 27 |
| 2. (Unt) | IgG | K | 31 | Vh5(DP73) | Jh3(a) | 18 |
| 3. (Tr) | IgA | K | 33 | Vh3(DP77) | Jh2 | 6 |
| 4. (Unt) | IgA | K | 30 | Vh4(DP65) | nd | 21 |
| 5. (Unt) | IgG | L | 23 | Vh3(DP49) | Jh6(b) | 30 |
| 6. (Unt) | IgG | K | 30 | Vh4(DP71) | Jh4(a) | 36 |
| 7. (Unt) | IgG | K | 25 | VH3(DP77) | Jh2 | 30 |
| 8. (Off) | IgA | L | 57 | Vh3(DP 46) | Jh3(b) | 21 |
| 9. (Off) | Ndᵃ | L | 80 | Vh3-21(DP77) | Jh6(c) | 24 |
| 10. (Unt) | IgG | K | 90 | Vh2(S12-12) | Jh4(a) | 33 |
| 11. (Sm) | IgA | K | 51 | Vh3-30(DP49) | Jh4(a) | 18 |
| 12. (Tr)** | IgG | L | 11 | Vh3-15(DP38) | Jh4(a) | 21 |
| 13. (Unt) | IgA | K | 70 | Vh3-8(DP58) | Jh4(a) | 27 |
| 14. (Off)*** | IgG | K | 67 | Vh3-30(DP49) | Jh4(b) | 24 |
| 15. (Unt) | IgG | K | 75 | Vh4-31(DP78) | Jh4(b) | 12 |
| 16. (Unt) | IgG | K | 22 | Vh1(DP88) | Jh4(b) | 36 |
| 17. (Unt) | IgG | K | 50 | Vh3-49(DP57) | Jh4(c) | 54 |
| 18. (Tr) | IgG | K | 41 | Vh5-51(DP73) | Jh4(b) | 15 |

*These patients were all diagnosed with myeloma; patients #8 and 14 were in relapse at the time their BM was obtained. Patient #10 died one month post-diagnosis. Their treatment status at the time the bone marrow sample was obtained is indicated. Patient 11 has smoldering myeloma, and remains untreated, for the samples analyzed here. Selection criteria for this study were that the patient was diagnosed with myeloma and that a fresh BM sample was available; no selection was applied for stage of disease or treatment status.
**This patient was in stable phase immediately prior to hematopoietic transplantation.
***This patient was first diagnosed in 1988 and is thus a long term survivor. In 1993/94, she had clonotypic DNA sequences detectable in her blood (6, Patient #3 in that study). The sequence of IgH VDJ transcripts in her plasma cells was determined at relapse for this study (in 1997) using single sorted BM plasma cells. The CDR3 sequence obtained was identical to that determined previously (6). All of her relapse plasma cells express this sequence.
ᵃ% PC = percent of plasma cells in the bone marrow sample used to derive the clonotypic sequence;
ND = not detectable by routine clinical methods;
Lt = light chain;
K = kappa;
L = lambda;
Unt = untreated;
Tr = treated; and
Off = off therapy.

TABLE 5

Clonotypic IgH CDR3 sequences and primers used for PSA

| codon 92 | (SEQ ID NOS: 12–29) FR3 | (SEQ ID NOS: 30–47) CDR3 |
|---|---|---|
| 01 | TGTGCTCAC | AAACTTATCACTGGTTGGGACGGTAGTAGT |
| 02 | TGTGCGACA | CAACACTACTATGATAGT |
| 03 | TGTGCGAGA | GATACCTATTATTATGGTTCAGGGAGTTATTCA |
| 04 | TGTGCGGGT | GGCACCACGTCCTCCCAGGGT |
| 05 | TGTGCGAAG | CTCGTGGTTGTGGCGGTGGAAGCTCTAACCCAT |
| 06 | TGTGCGAGG | GTCCCCATGAACTATGCTATAAGGGGAAACTTAGGT |
| 07 | TGTGCGACA | GAATGGTCGTACTTCTATGAAAGTTATTGGTTA |
| 08 | TGTGCGAGA | GACGGAAGCAGAGATGGCTACAACTCG |
| 09 | TGTGCGAGA | GGGGATGGTTCGGGAGAGATCTTT |
| 10 | TGTTCACAC | ACGCGTTTCATGCCTGCGGATGTGAACAACTTC |
| 11 | TGTGCGCCA | GTTCTTGCCAACTGGTTT |
| 12 | TGTACCACA | GCGTTCAGTGAGCCCTCCAGC |
| 13 | TGTGCGACA | GATCAAGATGACTATGGTGACTACGGGACC |
| 14 | TGTACGAGA | GTAAATCCTTTCTATGAAGGTAGTCGTTATCCCATA |
| 15 | TGCGCCACA | GATCCCTCTGAC |
| 16 | TGTGCGACA | GTAAATCCTTTCTATGAAGGTAGTCGTTATCCCATA |
| 17 | TGTACTAGA | GATAGGGAGGATACTGTAGTAGGAACAGTTACTATGGGCCGAATACCCACGGTT |
| 18 | TGTGCGAGA | CATTATCACGGTTAC |

TABLE 5-continued

Clonotypic IgH CDR3 sequences and primers used for PSA

| codon 92 | (SEQ ID NOS: 48–65) JH |
|---|---|
| 01 | TACTTTGACCAG.TGGGGC |
| 02 | TATATTGACTTC.TGGGGC |
| 03 | TACTGGTACTTCGATCTC.TGGGGC |
| 04 | CAGAGGTTGGAACTC.TGGGGC |
| 05 | GATAATCTTGATATT.TGGGGC |
| 06 | TCCATTGACTAC.TGGGGC |
| 07 | TTACCCTTTGACTTC.TGGGGC |
| 08 | GGTGTTTTTGATATC.TGGGGC |
| 09 | CCTTACTACTACTATCACATGGACGTC.TGGGGC |
| 10 | TTTGACTAC.TGGGGC |
| 11 | CGCCCCTTFGACCAC.TGGGGC |
| 12 | GACTACTACACGATGGACTTC.TGGGGC |
| 13 | TTFAACTCC.TGGGGC |
| 14 | TACTACTTTGGCFAC.TGGGGC |
| 15 | TACTTFGACCTC.TGGGGC |
| 16 | TACTACTTFGGCTAC.TGGGGC |
| 17 | AAATACTACTACTACCACCACATGGACGTC.TGGGGC |
| 18 | CGATCGGACGTC.TGGGGC |

Regions used as patient-specific CDR3 primers are highlighted in bold italics.

TABLE 6

Clonotypic B cells are frequent in the blood of myeloma patients

| Patient Status- Apr. 97 | # of sequential time points | % of cells that are clonotypic | | Absolute # × $10^9$/L Blood |
|---|---|---|---|---|
| | | of B cells | of PBMC | |
| 1. Tr | 5 | 69,99,91 95,62 | 24,3,14 10,18 | 0.1,0.35,0.09 0.05,0.11 |
| 2. Deceased | 2 | 74,74 | 19,31 | 0.17,0.15 |
| 3. Tr | 2 | 71,54 | 14,9 | 0.22,0.12 |
| 4. Allo Tsp | 4 | 45,46,46,62 | 9,9,10,19 | 0.12,0.08,0.06,0.11 |
| 5. Off | 3 | 91,40,73 | 18,8,16 | 0.24,0.1,0.21 |
| 6. Tr | 3 | 60,77,90 | 10,10,50 | 0.08,0.03,0.1 |
| 7. Deceased | 1 | 93 | 12 | 0.06 |
| 8. Deceased | 1 | 9 | 0.9 | 0.01 |
| 9. Tr | 1 | 52 | 7 | 0.09 |
| 11. Unt | 2 | 65,64 | 10,6 | 0.08,0.06 |
| 12. Auto Tsp | 2 | 46,64 | 15,7 | 0.16,0.13 |
| 13. Tr | 1 | 73 | 12 | 0.18 |
| 14. Tr | 2 | 28,90 | 8,21 | 0.03,0.08 |
| 15. Tr | 2 | 66,90 | 11,13 | 0.17,0.13 |
| 16. Tr | 1 | 56 | 13 | 0.17 |
| 17. Tr | 1 | 53 | 20 | 0.42 |
| 18. Tr | 2 | 68,49 | 20,18 | 0.61,0.39 |
| Mean | | 66 ± 4 | 14 ± 2 | 0.15 ± .02 |

Normal PBMC (15 donors)
  CD19+ PBMC (60 slides) <0.3%
Normal Plasma Cells (BM, 4 Donors)
  CD38$^{hi}$Ig+BMC (19 slides) <0.3%

Individual time points are listed sequentially in the table. #1 was slowly responding to melphalan (M) and dexamethasone (Dex), #2 had M/Dex, #3 is relapsing after treatment with M/prednisone (P), #4 was treated with M/P and then received an allogeneic transplant, #5 is being treated with M/P, #6 was treated with M/Decadron but did not respond, #7 received M/Dex, #8 was at a terminal stage of disease, #9 was newly diagnosed untreated, #11 has smoldering myeloma and remains untreated, #12 responded to VAD and was in plateau, and #13 was newly diagnosed untreated. Patient #14 was in relapse. Patients #15–18 were studied at diagnosis and/or during the first 1–2 cycles of first line therapy. Mean values are ±SE. For all samples, a minimum of 300 cells and frequently 500–1000 cells were viewed. In all cases, for in situ RT-PCR assays being performed on a given day, the patient-specific primers being tested each day on sorted myeloma B cells were also tested on B cells from normal donors to confirm their specificity. Every set of patient-specific primers has been tested on sorted B cells from at least 2 normal donors and on sorted CD19+ BMC from at least one normal donor. No amplification was detected in these normal donor controls.

References

Alberts B, Bray D, Lewis J, Raff M, Roberts K, Watson J: Molecular Biology of the Cell, third edition, Garland Publishing, Inc., New York, N.Y., 1995, Chapter 23.

Bakkus M H C, van Riet I, Van Camp B, Thielemann K: Evidence that the clonogenic cell in multiple myeloma originates from a pre-switched but somatically mutated B cell. Brit. J. Henatol. 87:68, 1994.

Barlogie B. Epstein J., Selvanayagam P., Alexanian R.: Plasma cell myeloma-new biological insights and advances in therapy. Blood 73: 865, 1989.

Berenson J, Wong R, Kim K, Brown N, Lichtenstein A: Evidence of peripheral blood B lymphocyte but not T lymphocyte involvement in multiple myeloma. Blood 70:1550, 1987.

Bergsagel D E: Treatment of plasma cell myeloma. Ann. Rev. Med. 30:431,1979

Bergsagel P L, Masellis Smith A, Szczepek A, Mant M J Belch A R, Pilarski L M: In multiple myeloma, clonotypic B lymphocytes are detectable among CD19+ peripheral blood cells expressing CD38, CD56 and monotypic immunoglobulin light chain. Blood 85:436, 1995.

Billadeau D, Blackstadt M, Greipp P, Kyle R A, Oken M M, Kay N, Van Ness B: Analysis of B-lymphoid malignancies using allele-specific polymerase chain reaction: A technique for sequential quantitation of residual disease. Blood 78:3021, 1991.

Billadeau D, Quam L, Thomas W, Kay M, Greipp P, Kyle R, Oken M M, Van Ness B: Detection and quantitation of malignant cells in the peripheral blood of multiple myeloma patients. Blood 80:1818, 1992.

Billadeau D, Ahmann G, Greipp P, van Ness B: The bone marrow of multiple myeloma patients contains B cell populations at different stages of differentiation that are clonally elated to the malignant plasma cell. J. Exp. Med. 178:1023, 1993.

Billadeau D, van Ness B, Kimlinger T, Kyle R A, O'Fallon W M, Greipp P R, Witzig T E: Clonal circulating cells are a common occurrence in plasma cell disorders: a comparison of MGUS, SMM and MM. Blood 86:58a, 1995.

Boccadoro M, Gavarotti P, Fossati G, Massaia M, Pilieri A, Durie B G M: Kinetics of circulating B lymphocytes in human myeloma. Blood 61:812, 1983.

Caligaris-Cappio F, Bergui L, Tesio L, Pizzolo G, Malavasi F, Chilosi M, Campana D, van Camp B, Janossy G: Identification of malignant plasma cell precursors in the bone marrow of multiple myeloma. J. Clin. Ivest. 76:1243, 1985.

Cao J., Vescio R A, Hong C H, Kim A., Lichenstein A K, Berenson J R: Identification of malignant cells in multiple myeloma bone marrow with immunoglobulin Vh gene probes by fluorescent in situ hybridization and flow cytometry. J Clin. Invest. 95:964, 1995.

Cao J, Vescio R A, Rettig M B, Hong C H, Kim A, Lee J C, Lichtenstein A K, Bersenson J R: A CD10-positive subset of malignant cells is identified in multiple myeloma using PCR with patient-specific immunoglobulin gene primers. Leukemia 9:1948, 1995.

Cassel A, Leibovitz N, Homstein L, Quitt M, Aghai E: Evidence for the existence of circulating monoclonal B-lymphocytes in multiple myeloma patients. Exp. Hematol. 18:1171,1990.

Chen B J, Epstein J: Circulating clonal lymphocytes in myeloma constitute a minor population of B cells. Blood 87:1972, 1996.

Coiradini P, Voena C, Astolfi M, Ladetto M, Tarella C, Boccadoro M, Pileri A: High dose sequential chemotherapy in multiple myeloma: residual tumor cells are detectable in bone marrow and peripheral blood cell harvests and after autografting. Blood 85:1596, 1995.

Corradini P, Voena C, Omede P, Astolfi M, Boccadoro M, Dalla-Favera R, Pileri A: Detection of circulating tumor cells in multiple myeloma by a PCR based method. Leukemia 7:1879, 1993. Chen and Epstein 1996.

Dreyfus F, Melle J, Quarre C, Pillier C: Contamination of peripheral blood by monoclonal B cells following treatment of multiple myeloma by high dose chemotherapy. Brit. J. Hematol. 85:411, 1993.

Mariette X, Fermand J-P, Brouet J-C: Myeloma cell contamination of peripheral blood stem cell grafts in patients with multiple myeloma treated by high dose therapy. Bone Marrow Transp. 14:47, 1994.

Gazitt U, Reading C, Lee J-H, Barlogie B, Vesole D, Jaganath S, Simonetti D, DiGuisto R, Schnell J, Rosen N R, Tricot G: Differential peripheral blood mobilization of tumor and normal hematopoietic progenitor cells (HPC) in multiple myeloma (MM). Blood 84:354a, 1994.

Greipp P R: Advances in the diagnosis and management of myeloma. Sem. Hematol. 29:24, 1992.

Hulin N, Conte P F, Pileri A: Biology of the human myeloma population. La Ricerca in Clinica e in Laboratorio 8:49, 1978.

Jensen G S, Mant M J, Belch A R, Berenson J R, Ruether B A, Pilarski L M: Selective expression of CD45 isoforms defines CALLA+ monoclonal B lineage cells in peripheral blood from myeloma patients as late stage B cells. Blood 78:711, 1991.

Mariette X, Fermand J-P, Brouet J-C: Myeloma cell contamination of peripheral blood stem cell grafts in patients with multiple myeloma treated by high dose therapy. Bone Marrow Transp. 14:47, 1994.

Nuovo G: PCR in situ Hybridization. New York, N.Y.: Raven Press, 1994.

Omede P, Boccadoro M, Fusaro A, Gallone G, Pileri A: Multiple myeloma: "early" plasma cell phenotype identifies patients with aggressive biological and clinical characteristics. Brit. J. Henatol. 85:504, 1993.

Owen R G, Child J A, Rawson A, Smith G M, Johnson R, Wood hear V, Elsworth A, Morgan G J: Detection of contaminating cells in PBMC harvests and the efficacy of CD34 selection in patients with multiple myeloma. Blood: 84:352a, 1994.

Palmer M., Belch A., Hanson J., Brox L.: *Reassessment of the relationship between M-protein decrement and survival in multiple myeloma. Br. J. Cancer* 59:110, 1989.

Pietersz G A, Li W J, Sutton V R, Burgess J, McKenzie I F C, Zola H, Trapani J A: In vitro and in vivo antitumor-activity of a chimeric anti-CD19 antibody. Cancer Immunol. Immunother. 41:53, 1995.

Pilarski L M, Mant M J, Ruether B A, Belch A: Severe deficiency of B lymphocytes in peripheral blood from multiple myeloma patients. J. Clin. Invest. 74:1301, 1984.

Pilarski L M, Ruether B A, Mant M J: Abnormal function of B lymphocytes from peripheral blood of multiple myeloma patients. I. Lack of correlation between the number of cells potentially able to secrete IgM and serum IgM levels. J. Clin. Invest. 75:2024, 1985.

Pilarski L M., Jensen G S.: Monoclonal circulating B cells in multiple myeloma: A continuously differentiating possibly invasive population as defined by expression of CD45 isoforms and adhesion molecules. Hematology/Oncology Clinics of North America 6:297, 1992.

Pilarski L M, Belch, A J: Circulating monoclonal B cells expressing p-glycoprotein may be a reservoir of multidrug resistant disease in multiple myeloma. Blood 83:724, 1994.

Pilarski L M., Masellis Smith A, Szczepek A., Mant M J, Belch A R: Circulating clonotypic B cells in the biology of myeloma. Speculations on the origin of multiple myeloma. Leuk. Lymphoma 18:179, 1996.

Sambrook J. Fritsch E F, Maniatis T. Molecular Cloning: A Laboratory Manual (2nd Ed.), Cold Spring Harbor Press, Cold Spring Harbor, N.Y., 1989, Volume 3.

Takashita M, Kosaka M, Goto T, Saito S: Cellular origin and extent of clonal involvement in multiple myeloma: genetic and phenotypic studies. Brit. J. Haematol. 87:735, 1994.

Taub R., Kirsch J. Morton C., Lenoir G., Swan D., Tronick S. Aaronson S., and Leder P. Translocation of the c-myc gene into the immunoglobulin heavy chain locus in human Burkitt lymphoma and murine plasmacytoma cells. Proc. Natl. Acad. Sci. U.S.A. 79:7837 (1982)

Rowley J D: Molecular cytogenetics: Rosetta Stone for understanding cancer—twenty-ninth G.H.A. Clowes Memorial Award Lecture. Cancer Res 50: 3816–25 (1990).

Vescio R A, Han E J, Lee J C, Wu, C H, Cao J, Shin J, Schiller G J, Rettig M B, Lichtenstein A K, Berenson J R: Quantitative comparison of multiple myeloma contamination in bone marrow harvest and leukaphereses autografts. Blood 86:234a, 1995.

Yameda M, Wasserman R, Lange B, Reichard B, Womer R, Rovera G: Minimal residual disease in childhood B-lineage lymphoblastic leukemia. N. Engl. J. Med. 323:448, 1990.

Zola H, Mcardle P J, Bradford T, Weedon H, Yasui H, Kurosawa Y: Preparation and characterization of a chimeric CD19 monoclonal antibody. Innunol. Cell Biol. 69:411, 1991.

U.S. Pat. No. 5,418,132 to Morley (1995).
U.S. Pat. No. 4,683,202 to Mullis (1987).
U.S. Pat. No. 5,436,144 to Stewart and Timm (1995).

We claim:

1. A method for detecting a target clonotypic nucleic acid rearrangement in hematopoietic cells from a subject having, or at risk of having, a hematopoietic neoplastic disorder comprising:
   a) isolating a hematopoietic neoplastic cell containing the target clonotypic nucleic acid rearrangement;
   b) amplifying a specific segment of the target nucleic acid containing the clonotypic rearrangement from said isolated hematopoietic neoplastic cell;
   c) determining the sequence of the amplified segment, thereby identifying a specific clonotypic nucleic acid rearrangement; and
   d) quantitatively detecting the presence of said specific clonotypic nucleic acid rearrangement in a second population of isolated intact hematopoietic cells derived from a subject having, or at risk of having, a neoplastic hematopoietic disorder, such that said target clonotypic nucleic acid rearrangement in said second population of isolated hematopoietic cells is detected.

2. The method of claim 1 wherein the hematopoietic cells are malignant cells.

3. The method of claim 2 wherein the hematopoietic cells are B cells or T cells.

4. The method of claim 1 wherein the hematopoietic cells are multiple myeloma cells.

5. The method of claim 1 wherein the clonotypic rearrangement is in an Ig gene locus.

6. The method of claim 1 wherein the clonotypic rearrangement is in a TCR gene locus.

7. The method of claim 1 wherein the clonotypic rearrangement is a chromosomal translocation.

8. The method of claim 1, wherein the amplifying is by PCR.

9. The method of claim 8 wherein cells bearing a clonotypic rearrangement are detected by direct labeling of a PCR product.

10. The method of claim 1 wherein cells bearing a clonotypic rearrangement are detected by nucleic acid hybridization to a PCR product.

11. The method of claim 8 wherein PCR primers for PCR specifically amplify the unique hypervariable regions of the IgH, k or 1 Ig gene, or of the TCR a, b, g or d chain.

12. The method of claim 8 wherein PCR primers for PCR are specific for the CDR1, CDR2 and/or the CDR3 region.

13. The method of claim 12 wherein the specific primers for the CDR1, CDR2 or CDR3 region are used in conjunction with a framework-specific consensus primer.

14. The method of claim 1, wherein said subject is being treated for a hematological malignancy, and wherein said hematopoietic neoplastic cell is isolated from said subject's blood or bone marrow.

15. The method of claim 1, wherein the specific clonotypic nucleic acid rearrangement is detected in cells destined for autologous transplantation.

16. The method of claim 1, wherein the presence of the specific clonotypic nucleic acid rearrangement is detected in intact hematopoietic cells.

17. The method of claim 1, wherein the presence of said specific clonotypic nucleic acid rearrangement is detected by determining the frequency of said rearrangement in said second population of isolated intact hematopoietic cells.

18. The method of claim 1, wherein said second population of intact hematopoietic cells consists of a single intact hematopoietic cell.

19. A method for determining the frequency of a target clonotypic nucleic acid rearrangement in hematopoietic cells from a subject having, or at risk of having, a hematopoietic neoplastic disorder consisting of:

a) isolating a hematopoietic neoplastic cell containing the target clonotypic nucleic acid rearrangement;

b) amplifying a specific segment of the target nucleic acid containing the clonotypic rearrangement from said isolated hematopoietic neoplastic cell;

c) determining the sequence of the amplified segment, thereby identifying a specific clonotypic nucleic acid rearrangement;

d) detecting the presence of said specific clonotypic nucleic acid rearrangement in an isolated intact hematopoietic cell derived from said subject; and e) detecting the presence of said specific clonotypic nucleic acid rearrangement in additional isolated intact hematopoietic cells, such that the frequency of said target clonotypic nucleic acid rearrangement in said second population of isolated hematopoietic cells is determined.

* * * * *